United States Patent
Clarke et al.

(10) Patent No.: US 9,533,078 B2
(45) Date of Patent: Jan. 3, 2017

(54) MEDICAL DEVICES CONTAINING THERAPEUTIC AGENTS

(75) Inventors: John Clarke, Galway (IE); Tim O'Connor, Galway (IE); Barry J. O'Brien, Galway (IE); David McMorrow, Galway (IE); Jan Weber, Maastricht (NL); Aiden Flanagan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1209 days.

(21) Appl. No.: 13/000,594

(22) PCT Filed: Jun. 19, 2009

(86) PCT No.: PCT/US2009/047899
§ 371 (c)(1),
(2), (4) Date: Feb. 16, 2011

(87) PCT Pub. No.: WO2009/158276
PCT Pub. Date: Dec. 30, 2009

(65) Prior Publication Data
US 2011/0130829 A1    Jun. 2, 2011

Related U.S. Application Data

(60) Provisional application No. 61/172,567, filed on Apr. 24, 2009, provisional application No. 61/075,529, filed on Jun. 25, 2008.

(51) Int. Cl.
*A61F 2/06* (2013.01)
*A61L 31/16* (2006.01)
(Continued)

(52) U.S. Cl.
CPC ............ *A61L 31/16* (2013.01); *A61L 27/30* (2013.01); *A61L 27/54* (2013.01); *A61L 29/10* (2013.01);
(Continued)

(58) Field of Classification Search
CPC ........................................... A61F 2/82
(Continued)

(56) References Cited

U.S. PATENT DOCUMENTS 4,863,538 A    9/1989 Deckard
5,733,925 A    3/1998 Kunz et al.
(Continued)

FOREIGN PATENT DOCUMENTS

EP    1810665 A1    7/2007
JP    2006175017    7/2006
(Continued)

OTHER PUBLICATIONS

J.-Z. Chen et al, "NMR characterization of paclitaxel/poly(styrene-isobutylene-styrene) formulations", International Journal of Pharmaceutics, 305 (2005) 129-144.
(Continued)

*Primary Examiner* — Jacqueline Woznicki
(74) *Attorney, Agent, or Firm* — Seager, Tufte & Wickhem, LLP

(57) ABSTRACT

The present invention pertains to implantable or insertable medical devices which comprise a substrate and one or more therapeutic-agent-containing regions contain one or more therapeutic agents. In various aspects of the invention, one or more characteristics of such therapeutic-agent-containing regions are controlled. Further aspects of the invention relate to methods of forming such devices and to methods of using such devices.

25 Claims, 9 Drawing Sheets

(51) Int. Cl.
  *A61L 27/30* (2006.01)
  *A61L 27/54* (2006.01)
  *A61L 29/10* (2006.01)
  *A61L 29/16* (2006.01)
  *A61L 31/08* (2006.01)
  *A61L 31/14* (2006.01)
  *A61F 2/82* (2013.01)

(52) U.S. Cl.
  CPC .............. *A61L 29/16* (2013.01); *A61L 31/082* (2013.01); *A61L 31/146* (2013.01); *A61F 2/82* (2013.01); *A61F 2250/0014* (2013.01); *A61F 2250/0025* (2013.01); *A61F 2250/0026* (2013.01); *A61F 2250/0037* (2013.01); *A61F 2250/0067* (2013.01); *A61L 2300/416* (2013.01); *A61L 2300/63* (2013.01)

(58) Field of Classification Search
  USPC ........................................................ 623/1.42
  See application file for complete search history.

(56) References Cited

U.S. PATENT DOCUMENTS

| | | | |
|---|---|---|---|
| 5,869,170 | A | 2/1999 | Cima |
| 6,221,153 | B1 | 4/2001 | Castor et al. |
| 6,379,381 | B1* | 4/2002 | Hossainy et al. ............ 623/1.42 |
| 6,379,383 | B1 | 4/2002 | Palmaz |
| 6,545,097 | B2 | 4/2003 | Pinchuk et al. |
| 6,558,733 | B1 | 5/2003 | Hossainy |
| 6,709,379 | B1 | 3/2004 | Brandau |
| 6,740,077 | B1 | 5/2004 | Brandau |
| 6,803,070 | B2 | 10/2004 | Weber |
| 6,913,762 | B2 | 7/2005 | Caplice |
| 2002/0120326 | A1* | 8/2002 | Michal ........................ 623/1.15 |
| 2004/0107019 | A1 | 6/2004 | Keshavmurthy |
| 2004/0243133 | A1 | 12/2004 | Materna |
| 2005/0070989 | A1 | 3/2005 | Lye |
| 2005/0106212 | A1 | 5/2005 | Gertner |
| 2005/0181141 | A1 | 8/2005 | Flanagan |
| 2005/0228477 | A1* | 10/2005 | Grainger ................... A61F 2/91 623/1.11 |
| 2005/0233062 | A1 | 10/2005 | Hossainy et al. |
| 2005/0266040 | A1 | 12/2005 | Gerberding |
| 2006/0111772 | A1 | 5/2006 | White |
| 2006/0127443 | A1 | 6/2006 | Helmus et al. |
| 2006/0128739 | A1 | 6/2006 | Maryanoff et al. |
| 2006/0129215 | A1 | 6/2006 | Helmus et al. |
| 2006/0129228 | A1 | 6/2006 | Golesworthy |
| 2006/0134168 | A1 | 6/2006 | Chappa et al. |
| 2006/0171985 | A1 | 8/2006 | Richard et al. |
| 2007/0212394 | A1 | 9/2007 | Reyes et al. |
| 2007/0224235 | A1 | 9/2007 | Tenney et al. |
| 2008/0147177 | A1 | 6/2008 | Scheuermann et al. |
| 2009/0028785 | A1 | 1/2009 | Clarke |
| 2009/0123521 | A1 | 5/2009 | Weber et al. |
| 2010/0272773 | A1 | 10/2010 | Kangas et al. |

FOREIGN PATENT DOCUMENTS

| | | | |
|---|---|---|---|
| WO | 00/32238 | A1 | 6/2000 |
| WO | 2004037469 | A1 | 5/2004 |
| WO | 2005049520 | A2 | 6/2005 |
| WO | 2009/018035 | A2 | 2/2009 |

OTHER PUBLICATIONS

S. Hurrell et al., "The effect of initial polymer morphology on the degradation and drug release from polyglycolide", Biomaterials 23 (2002) 2401-2409.

In-Hyun Lee et al., "Stable paclitaxel formulations in oily contrast medium", Journal of Controlled Release, 102 (2005) 415-425.

B.C. Hancock et al., "What is the True Solubility Advantage for Amorphous Pharmaceuticals?" Pharmaceutical Research 17 (2000) 397-404.

* cited by examiner

MEDICAL DEVICES CONTAINING THERAPEUTIC AGENTS

RELATED APPLICATIONS

This application claims priority from U.S. Provisional Application 61/075,529 filed Jun. 25, 2008 and U.S. Provisional Application 61/172,567 filed Apr. 24, 2009, which are incorporated by reference in their entirety herein.

TECHNICAL FIELD

This invention relates to medical devices that release therapeutic agents.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

For example, in recent years, drug eluting coronary stents, which are commercially available from Boston Scientific Corp. (TAXUS and PROMUS), Johnson & Johnson (CYPHER) and others, have been widely used for maintaining vessel patency after balloon angioplasty. These products are based on metallic expandable stents with polymer coatings that release anti-restenotic drugs at a controlled rate and total dose.

Therapeutic agents have also been delivered to vessel walls using balloons. For example, there have been clinical trials showing that in-stent restenosis can be treated using a balloon having a sprayed coating of pure paclitaxel.

SUMMARY OF THE INVENTION

The present invention pertains to implantable or insertable medical devices which comprise a substrate and one or more therapeutic-agent-containing regions.

In various aspects of the invention, one or more characteristics of such therapeutic-agent-containing regions are controlled, for example, selected from one or more of the following, among others: the composition of such regions, the crystalline form of such regions, the size of such regions, the shape of such regions, the spatial distribution of such regions over the substrate, the total dose associated with such regions, the rate of drug release and/or tissue uptake of drug associated with such regions, and the adhesion of such regions to the underlying substrate.

Other aspects of the invention relate to methods of forming such devices and to methods of using such devices.

These and other aspects, as well as various embodiments and advantages of the present invention will become immediately apparent to those of ordinary skill in the art upon review of the Detailed Description and Claims to follow.

DETAILED DESCRIPTION

Figure 1:
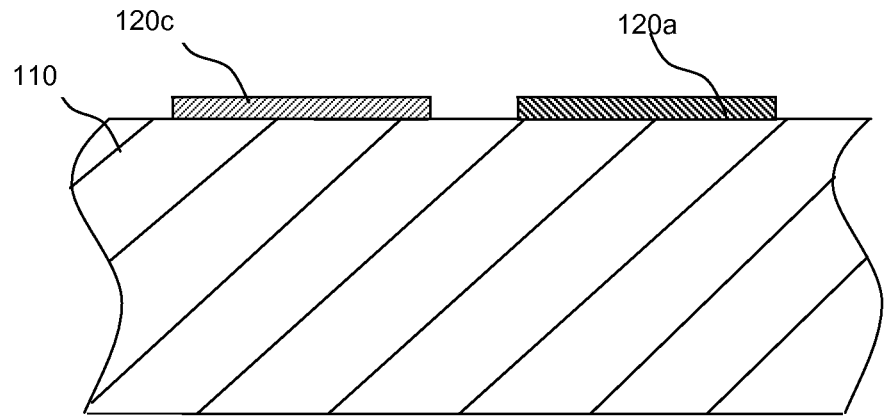
FIGS. 1-7, 9 and 10 are schematic partial cross-sections of medical devices in accordance with various embodiments of the present invention.

The present invention pertains to implantable or insertable medical devices which comprise a substrate and one or more regions (also referred to herein as "material regions" or "regions of material") that comprise a therapeutic agent (also referred to herein as "therapeutic-agent-containing regions"). In various aspects of the invention, one or more characteristics of such therapeutic-agent-containing regions are controlled as discussed in detail below.

"Therapeutic agents," "drugs," "biologically active agents," "pharmaceutically active agents," and other related terms may be used interchangeably herein.

Examples of medical devices benefiting from the various aspects of the present invention vary widely and include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglielmi detachable coils and metal coils), septal defect closure devices, drug depots that are adapted for placement in an artery for treatment of the portion of the artery distal to the device, myocardial plugs, patches, pacemakers, leads including pacemaker leads, defibrillation leads and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, or other devices that are implanted or inserted into the body and from which therapeutic agent is released.

The medical devices of the present invention include, for example, implantable and insertable medical devices that are used for systemic treatment or diagnosis, as well as those that are used for the localized treatment or diagnosis of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, brain, lungs, trachea, esophagus, intestines, stomach, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Subjects are vertebrate subjects, more typically mammalian subjects including human subjects, pets and livestock.

Substrate materials for the medical devices of the present invention may vary widely in composition and are not limited to any particular material. They can be selected from a range of biostable materials (i.e., materials that, upon placement in the body, remain substantially intact over the anticipated placement period for the device) and biodisintegrable materials (i.e., materials that, upon placement in the body, are dissolved, biodegraded, resorbed, and/or otherwise removed from the placement site over the anticipated placement period), including (a) organic materials (i.e., materials containing organic species, typically 50 wt % or more, for example, from 50 wt % to 75 wt % to 90 wt % to 95 wt % to 97.5 wt % to 99 wt % or more) such as polymeric materials (i.e., materials containing polymers, typically 50 wt % or more polymers, for example, from 50 wt % to 75 wt % to 90 wt % to 95 wt % to 97.5 wt % to 99 wt % or more) and biologics, (b) inorganic materials (i.e., materials containing inorganic species, typically 50 wt % or more, for example, from 50 wt % to 75 wt % to 90 wt % to 95 wt % to 97.5 wt % to 99 wt % or more), such as metallic materials (i.e., materials containing metals, typically 50 wt % or more, for example, from 50 wt % to 75 wt % to 90 wt % to 95 wt % to 97.5 wt % to 99 wt % or more) and non-metallic inorganic materials (i.e., materials containing non-metallic inorganic materials, typically 50 wt % or more, for example, from 50 wt % to 75 wt % to 90 wt % to 95 wt % to 97.5 wt % to 99 wt % or more) (e.g., carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others), and (c) hybrid materials (e.g., hybrid organic-inorganic materials, for instance, polymer/metallic inorganic and polymer/non-metallic inorganic hybrids).

Specific examples of inorganic non-metallic materials may be selected, for example, from materials containing one or more of the following: metal oxide ceramics, including aluminum oxides and transition metal oxides (e.g., oxides of titanium, zirconium, hafnium, tantalum, molybdenum, tungsten, rhenium, iron, niobium, iridium, etc.); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based ceramic-like materials such as carbon nitrides.

Specific examples of metallic materials may be selected, for example, from metals such as gold, iron, niobium, platinum, palladium, iridium, osmium, rhodium, titanium, tantalum, tungsten, ruthenium, and magnesium, among others, and alloys such as those comprising iron and chromium (e.g., stainless steels, including platinum-enriched radiopaque stainless steel), niobium alloys, titanium alloys, alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium, zinc and/or iron (including their alloys with combinations of each other and Ce, Ca, Zr, Li, etc., for example, alloys containing magnesium and one or more of Fe, Ce, Ca, Zn, Zr and Li, alloys containing iron and one or more of Mg, Ce, Ca, Zn, Zr and Li, alloys containing zinc and one or more of Fe, Mg, Ce, Ca, Zr and Li, etc.), among others.

Specific examples of organic materials include polymers (biostable or biodisintegrable) and other high molecular weight organic materials, and may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, and glycosaminoglycans such as hyaluronic acid; as well as blends and further copolymers of the above.

In some embodiments, therapeutic-agent-containing regions are disposed within depressions in the surface of a substrate. Depressions in accordance with the present invention (and thus the therapeutic-agent-containing regions that can at least partially fill them) may come in a variety of shapes and sizes. Examples include depressions whose lateral dimensions (e.g., length and width, diameter, etc) are of similar scale, for instance, polygonal (e.g., triangular, rectangular, pentagonal, etc.), circular and oval depressions, as well as various other regular and irregular depressions of various shapes and sizes. Multiple depressions can be provided in a near infinite variety of arrays. Further examples of depressions include elongated depressions whose length significantly exceeds its width (e.g., trenches and valleys), which may be linear, which may be formed from segments whose direction undergoes an angular change (e.g., zigzag and wavy structures), which may intersect at right angles (or other angles) thereby forming grids, as well as other regular and irregular elongated structures.

As noted above, in addition to a substrate, the implantable or insertable medical devices of the invention include one or more therapeutic-agent-containing regions.

The therapeutic-agent-containing regions may contain, for example, from 1 wt % or less to 2 wt % to 5 wt % to 10 wt % to 25 wt % to 50 wt % to 75 wt % to 90 wt % to 95 wt % to 97.5 wt % to 99 wt % or more of one or more therapeutic agents. Examples of materials other than therapeutic agents which can be used to form the therapeutic-agent-containing regions include materials that serve as binders, matrices, diluents, fillers, etc. for the therapeutic agent (collectively referred to herein as "excipients"). Examples of such materials include various organic materials, which may be selected, for example, from those listed above, among others. In other embodiments, the therapeutic-agent-containing regions are substantially pure (i.e., 95 wt % or more of a given therapeutic agent).

A wide variety of therapeutic agents can be employed in conjunction with the medical devices of the present invention including those used for the treatment of a wide variety of diseases and conditions (i.e., the prevention of a disease or condition, the reduction or elimination of symptoms associated with a disease or condition, or the substantial or complete elimination of a disease or condition). Therapeutic agents include non-genetic therapeutic agents, genetic therapeutic agents, and cells. Therapeutic agents may be used singly or in combination.

Exemplary therapeutic agents for use in connection with the present invention include: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists, (hh) iron chelating agents including siderophores such as hydroxamates, ethylenediamine tetra-acetic acid (EDTA) and its analogs, and catechols.

Therapeutic agents also include taxanes such as paclitaxel (including particulate forms thereof, for instance, protein-bound paclitaxel particles such as albumin-bound paclitaxel nanoparticles, e.g., ABRAXANE), sirolimus, everolimus, biolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, biolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Numerous additional therapeutic agents useful for the practice of the present invention are also disclosed in U.S. Pat. No. 5,733,925 to Kunz, the entire disclosure of which is incorporated by reference.

Figure 13:
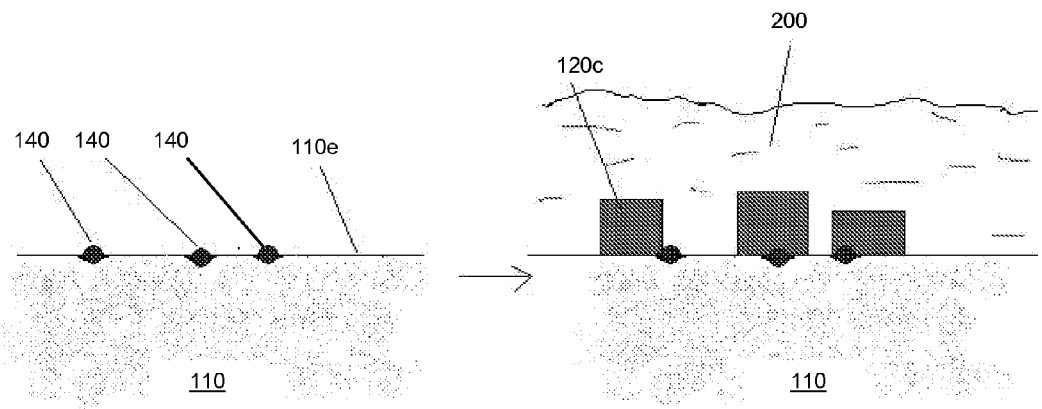
FIG. 13 is a schematic illustration of a process for forming drug crystals at the surface of a medical device, in accordance with an embodiment of the present invention.

In some embodiments, the therapeutic-agent-containing regions if the invention are in the form of layers. Layers can be provided over an underlying substrate at a variety of locations, and in a variety of shapes. As used herein, a "layer" of a given material is a region of that material whose thickness is small compared to both its length and width. As used herein a layer need not be planar, for example, taking on the contours of an underlying substrate. A layer can be discontinuous, providing only partial coverage of the underlying substrate. For example, a patterned layer may consist of therapeutic-agent-containing regions (e.g., dispersed particles) which are not in contact with one another (see, e.g., FIGS. 13, 16 and 17 discussed below). Terms such as "film," "layer" and "coating" may be used interchangeably herein.

Therapeutic-agent-containing layer thicknesses may vary widely, typically ranging from 10 nm or less to 25 nm to 50 nm to 100 nm to 250 nm to 500 nm to 1000 nm (1 µm) to 2.5 µm 5 µm to 10 µm or more in thickness. Individual layer thickness may be essentially constant over the entire substrate, that is, within a certain range from the average thickness, for example, the variation may be ranging from +/−1 nm to +/−5 nm to +/−20 nm to +/−100 nm. In some embodiments, individual layer thickness over the entire substrate ranges from ±25% of the average thickness. On the other hand, in some embodiments, the individual layer thickness may vary substantially along the substrate, ranging from as thin as 10 nm at one place to more then several micrometers at other places.

In certain embodiments, it is desirable to provide a discontinuous layer of therapeutic-agent-containing material on a medical device substrate. Such a discontinuous layer may comprise a first area that corresponds to one or more regions of therapeutic-agent-containing material which cover the substrate and a second area which does not cover the substrate, thereby leaving portions of the substrate bare. For example, the first area may comprise from 5% to 10% to 25% to 50% to 75% to 90% to 95% of the total area over which the discontinuous layer lies and the second area may comprise the remainder of the area.

Such embodiments may be desirable, for instance, where a release regulating layer (e.g., a nanoporous layer, biodisintegrable layer, etc.) is provided over the therapeutic-agent-containing material to regulate release, but where it is desirable to have contact between the release regulating layer and the substrate to enhance adhesion of the release regulating layer to the device.

As seen below, in some embodiments, at least 90% of the first area covering the substrate corresponds to numerous regions of therapeutic-agent-containing material (which may be referred to herein as "particles," "dots", etc.) having a width less than 100 µm (and in some embodiments having a length and a width that are each less than 100 µm), preferably less than 50 µm. In certain of these embodiments, many regions of therapeutic-agent-containing material are formed, for example, >100, >1000, or more regions per mm². In certain of these embodiments, at least 90 wt % (e.g., from 90 to 95 to 97 to 99 to 100 wt %) of the therapeutic-agent-containing material is provided in regions that are less than 100 µm in length, width and height, more preferably less than 50 µm in length, width and height (e.g., 5 to 50 µm).

Distinct regions of therapeutic-agent-containing material may be associated with the surface of a substrate using any suitable method. These methods include those whereby distinct regions of therapeutic-agent-containing material are formed over (including on) the substrate surface and/or within depressions in the substrate surface, among others.

For example, distinct regions may be formed by selective masking, followed by deposition of a continuous layer of therapeutic-agent-containing material, followed by mask removal. As another example, distinct regions of therapeutic-agent-containing material may formed by first depositing a continuous layer of therapeutic-agent-containing material, followed by selective removal of the material (e.g., using laser ablation). As yet another example, distinct regions of therapeutic-agent-containing material may be formed by direct deposition techniques.

In each technique, the therapeutic-agent-containing material may be formed from substantially pure therapeutic agent or may contain one or more excipients.

Methods of depositing a layer of therapeutic-agent-containing material include methods in which the substrate is contacted with a liquid that comprises a solvent, one or more therapeutic agents (e.g., in dissolved form or in dispersed particulate form) and any optional excipients, followed by solvent removal and further processing, as desired. Methods of depositing a layer of therapeutic-agent-containing material further include methods in which dry or semi-dry therapeutic-agent-containing particles (which contain one or more therapeutic agents and any optional excipients) are deposited on the substrate.

This preceding methods may be implement, for example, through spray coating, ink jet droplet deposition, ultrasonic spray coating, electrohydrodynamic coating, dipping, roll-coating, micro-contact printing, nanopipetting, dip pen nanolithography, and manual particle placement, among other methods.

Figure 15:
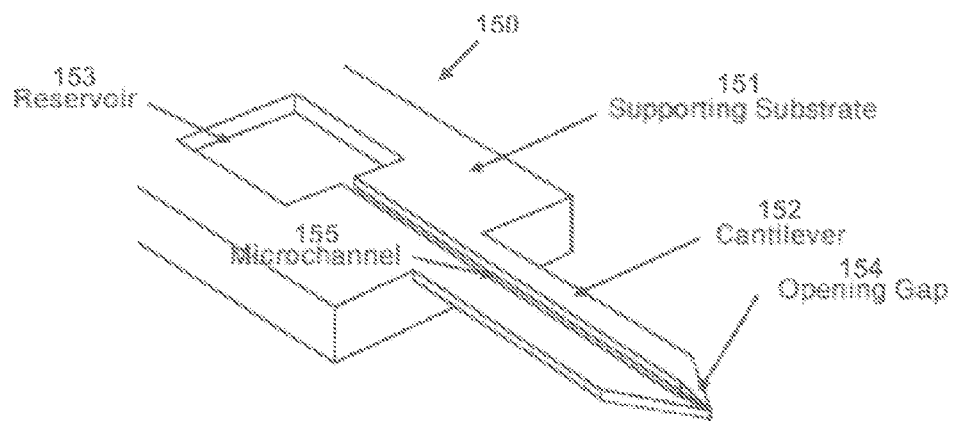
FIG. 15 is a partial schematic diagram of a printing device, in accordance with the prior art.

One specific example of an instrument by which arrays of small drops of therapeutic-agent-containing fluid, for instance in femtoliter ($10^{-15}$ L) and attoliter ($10^{-18}$ L) volumes (wherein 1 femtoliter corresponds to a drop<1 micron in diameter) can be directly deposited on a device surface is the Nano eNabler™ from Bioforce Nanosciences, Inc., Ames, Iowa, USA, the stylus of which is illustrated in FIG. 15, and includes a supporting structure 151 and associated cantilever 152, as well as a reservoir 153, and a microchannel 155 that leads to an opening gap 154. When the reservoir 153 is filled, a microfluidics technique is used to transfer liquid along microchannel 155 to the opening gap 154. This produces a drop at the tip of the cantilever 152. When brought into contact with a surface, a drop of liquid is deposited on the surface. Nano eNabler™ systems generally contain an array of such cantilevered openings 154 such that multiple drops are deposited simultaneously.

The Nano eNabler™ system can be used in accordance with the invention to deposit drops of a drug-containing liquid on a medical device substrate. Upon evaporation of the volatile component(s) of the drops (e.g., volatile solvents and/or non-solvents), drug particles are formed on the substrate surface. The amorphousness/crystallinity of the drug particles may be controlled as described elsewhere herein, if desired. The array of drops can be precisely spaced, leading to an array of precisely spaced drug-containing regions on a device surface. The drop size (and thus volume) is highly repeatable such that for a liquid of known drug concentration, the amount of drug deposited can be determined based on the number of drops deposited.

For deposition on a cylindrical medical device substrate (e.g., a stent, balloon, etc.), the substrate can be mounted on a mandrel. The stylus may be mounted on a precise motion stage, allowing the stylus to be precisely positioned relative to the substrate (e.g. relative to the struts of a stent).

Drop deposition systems such as the Nano eNabler™ can also be used to create tiny wells (depressions) of diameter down to 1 micron or less in the surface of the substrate by depositing drops of liquid that are capable of etching the substrate material on the substrate (e.g., drops of acidic liquid on a metallic substrate, etc.). Because the thus-etched wells are precisely located as a result of the geometry of the openings in the stylus, the stylus (or one like it) can subsequently be used to deposit drops of drug-containing fluid into the wells.

As previously indicated, in some embodiments, the therapeutic-agent-containing regions of the invention are covered with a layer that may further regulate the release of the therapeutic agent (referred to herein as a "release regulating layer"). The layer may be, for example, biostable, biodisintegrable, or partially disintegrable. The layer may be formed, for example, from organic materials, inorganic materials (e.g., a metallic or non-metallic inorganic material or a combination thereof), or hybrid organic-inorganic materials, such as those described above for use as substrate materials, among others.

Examples of materials that can regulate release include soluble metal oxides such as those described in WO 2005/049520 to Cunningham et al. and in Ser. No. 60/951,280. Release can be controlled by the gradual release of drug molecules from the oxide surface (e.g., by breakdown of hydrogen bonds or other mechanism) or by using the soluble oxide as a semi-permeable barrier to control the release of the drug. Specific examples of soluble metal oxides in water include highly soluble oxides such as potassium oxide and sodium oxide, less soluble oxides such as magnesium oxide and calcium oxide, and slowly dissolvable oxides such as aluminum oxide, iron oxide and silicon dioxide.

As with the therapeutic-agent-containing layers, thicknesses for release regulating layers may vary widely, typically ranging from 10 nm or less to 25 nm to 50 nm to 100 nm to 250 nm to 500 nm to 1000 nm (1 μm) to 2.5 μm 5 μm to 10 μm or more in thickness.

In some embodiments, the release regulating layer is a nonporous layer, for example, where the layer is at least partially biodisintegrable (e.g., a non-porous biodisintegrable layer or a non-porous layer formed from a combination of biostable and biodisintegrable materials that yields a porous biostable layer in vivo).

In some embodiments, the release regulating layer is a porous layer, for example, a nanoporous layer or a macroporous layer. In accordance with the International Union of Pure and Applied Chemistry (IUPAC), a "nanopore" is a pore having a width that does not exceed 50 nm (e.g., from 0.5 nm or less to 1 nm to 2.5 nm to 5 nm to 10 nm to 25 nm to 50 nm). As used herein, nanopores include "micropores," which are pores having a width that does not exceed 2 nm, and "mesopores," which are range from 2 to 50 nm in width. As used herein, "macropores" are larger than 50 nm in width and are thus not nanopores. As used herein a "porous" layer is a layer that contains pores. A "nanoporous layer" is a layer that contains nanopores. A "macroporous layer" is a layer that contains macropores.

Organic (polymeric and non-polymeric) and inorganic (metallic and non-metallic) nanoporous layers may be formed, for example, as described in U.S. Ser. No. 60/857,849 filed Nov. 9, 2006, Pub. No. US 2006/0129215 to Helmus et al., Pub. No. US 2006/0127443 to Helmus et al., Pub. No. US 2006/0171985 to Richard et al. and WO/2009/018035 to Weber et al.

As a specific example, a porous layer of a biostable metal such as tantalum or gold or a porous or non-porous layer of a biodisintegrable metal such as iron, magnesium or zinc may be deposited, among many other materials, using a system available from Mantis Deposition Ltd., Thame, Oxfordshire, United Kingdom. The system includes a high-pressure magnetron sputtering source which is able to generate particles from a sputter target with as few as 30 atoms up to those with diameters exceeding 15 nm. The size of the nanoparticles is affected by several parameters, including the nanoparticle material, the distance between the magnetron surface and the exit aperture (e.g., larger distances have been observed to create larger nanoparticles), gas flow (e.g., higher gas flows have been observed to create smaller nanoparticle sizes), and gas type (e.g., helium has been observed to produce smaller particles than argon). For a particular setting, the size distribution can be measured using a linear quadrapole device placed after the exit aperture of the magnetron chamber. The quadrapole device can also be used in-line to select a narrow nanoparticle size range for deposition. Systems like the Mantis Deposition Ltd. system are capable of producing particle streams, a large fraction of which (e.g., 40% to 80%) have a charge of one electron. Consequently, a magnetic field or a secondary electric field can be used to separate particles of similar weight from one another (because lighter particles are deflected to a greater degree in a given field than are the larger particles of the same charge). The above Mantis Deposition Ltd. system is thus able to produce charged particle streams with a very narrow mass distribution. Moreover, it is possible to accelerate the negatively charged particles onto a positively biased surface in order to impact the particles on the surface with elevated kinetic energy. A positively biased grid may also be used to accelerate the particles, allowing the particles to pass through holes in the grid and impinge on the surface. By altering the bias voltage from low to high values the deposited film changes from porous loosely bound nanoparticles to a solid film of metal. A system similar to the Mantis system can be obtained from Oxford Applied Research, Witney, Oxon, UK. Such processes are room temperature processes. Using these and similar systems, thin metallic layers may be deposited on a variety of substrates.

Without wishing to be bound by theory, when nanoparticles are accelerated towards a surface, melting can be induced upon landing by imparting them with sufficient kinetic energy. For example, where charged nanoparticles are accelerated using an electric field, a low applied voltage will create a small electric field which lands them on the substrate with little or no thermal effects. Higher applied voltages, however, will result in greater field strengths, which if sufficiently great will result in a transformation of kinetic energy into heat in an amount sufficient to melt the nanoparticles slightly together, leaving gaps between the particles. Even higher field strengths will solidify the individual particles into a solid material without gaps. In some embodiments, adhesion of the nanoparticles to the substrate, to the drug and/or to one another each other can be tuned (e.g., by the extent of acceleration), and structures can be made that are, for example, tough and adherent or soft and friable. In addition to field strength, the size distribution of the nanoparticles has a large effect on the pore-size distribution, with larger particles creating larger pores, which pore sizes can be tailored through the adjustment of field strength. Sustained drug release is promoted by creating a uniform porosity throughout the nanoporous layer, which will depend upon both the initial size of the particles as well as upon the melting effect that arises from the field strength.

When using a system like the Mantis Deposition Ltd. system, it has been found that the bias voltage (which may vary, for example, from 10 V to 20,000 V) and the particle size (which may vary, for example, from 0.7 nm to 25 nm) has a significant effect upon drug release, with higher voltages and smaller particle sizes yielding coatings with reduced drug release.

As another example, charged nanoparticles may be accelerated onto a therapeutic-agent-coated structure using a technique like that described in U.S. Pat. No. 6,803,070 to Weber with an electric field strength that is sufficiently great to fuse the microparticles to one another, but which is not so great as to eliminate the porosity.

Due to the fact that the amount of energy needed to melt the individual nanoparticles in the foregoing techniques is relatively low compared to the energy needed to increase the bulk temperature of underlying therapeutic-agent-coated substrate, the preceding processes are effectively performed at or near room temperature.

It is further noted that systems can be created which provide a changing secondary field (e.g., an electric or magnetic field that acts to deflect/bend the particle stream created by a primary electric or magnetic field). For example, such a system can induce a continuously changing impact direction at a substrate (e.g., by bending the particle stream). Such as system is suitable for the coating of complex 3-D structures, for example, allowing the charged particles to strike the substrate at varying angles, resulting better coverage.

It may also be desirable to change the orientation of the therapeutic-agent-coated substrate relative to the charged particle stream. For example, a tubular medical device such as a stent may be axially rotated (and, optionally, reciprocated longitudinally, e.g., where the size of the charged particle stream is small relative to the substrate and/or where it is non-uniform) while exposing it to the charged particle stream.

As noted above, in various aspects, one or more characteristics of the therapeutic-agent-containing regions of the invention are controlled. In this regard, various aspects of the invention will now be discussed which pertain to the crystallinity of the therapeutic-agent-containing regions or lack thereof (amorphousness). Further characteristics which may be controlled, including the size and shape of such regions, adhesion of such regions to the substrate, the spatial distribution of such regions over the substrate, as well as the total dose, the rate of drug release and/or tissue uptake of drug associated with such regions, among other characteristics, are also discussed below.

With regard to crystallinity, in some embodiments, implantable or insertable medical devices are provided, which comprise a substrate and one or more regions that comprise a therapeutic agent in a predominantly crystalline form (also referred to herein as "crystalline regions").

In some embodiments, implantable or insertable medical devices are provided, which comprise a substrate and one or more regions that comprise a therapeutic agent in a predominantly amorphous form (also referred to herein as "amorphous regions").

In some embodiments, implantable or insertable medical devices are provided, which comprise a substrate and one or more first regions that comprise a first therapeutic agent in a predominantly crystalline form and one or more second regions that comprise a second therapeutic agent in a predominantly amorphous form. In these embodiments, the first and second therapeutic agents may be the same or different. As a specific example, an anti-platelet/anti-coagulant drug such as clopidogrel or heparin may be provided on a vascular stent in crystalline form to provide longer term thrombus resistance, whereas an anti-restenotic drug such as paclitaxel or everolimus may be in amorphous form to provide shorter term resistance to smooth muscle cell proliferation.

Embodiments of the invention relating to medical devices that comprise distinct crystalline and amorphous regions are in contrast to typical medical devices in which the drug is in crystalline form, amorphous form, or somewhere in between, with no substantial variation in drug crystallinity along the surface of the device.

As is well known, the constituent atoms (e.g., neutral atoms, ions) or molecules in a crystalline material are arranged in a regularly ordered, repeating pattern extending in three spatial dimensions. As is also well known, the constituent atoms or molecules in an amorphous material are not regularly ordered to any significant degree. Whether or not a material is in a predominantly crystalline state or a predominantly amorphous state can be measured by techniques such as SEM imaging, X-ray diffraction, or Differential Scanning calorimetry (DSC). For example, a predominantly crystalline material can be identified by regular geometric shapes such as polyhedrons, spheres, and so forth, which may be observed, for instance, using microscopic techniques such as SEM. A predominantly amorphous material can be identified, on the other hand, by disordered structure and a lack of geometric shape. Particles associated with crystalline materials may be much larger than particles associated with amorphous materials.

Amorphous pharmaceuticals are markedly more soluble than their crystalline counterparts. B. C. Hancock et al., *Pharmaceutical Research* 17 (2000) 397-404. Without wishing to be bound by theory, it is believed that amorphous materials generally exist in a high energy state and are therefore relatively unstable. Crystalline materials, on the other hand, generally exist in a low energy state and are therefore relatively stable. Consequently, as a general rule, the more crystalline one makes a given therapeutic agent, the slower that therapeutic agent will dissolve and be released. On the other hand, the more amorphous one makes the therapeutic agent, the faster the therapeutic agent will dissolve and be released. These characteristics are used in the present invention to modulate drug release from medical devices.

In accordance with an aspect of the invention, at least one material region comprising a first therapeutic agent in a predominantly crystalline form (i.e., at least one "crystalline region") can be used to provide longer term release of a first therapeutic agent, while at least one material region comprising a second therapeutic agent in a predominantly amorphous state (i.e., a least one "amorphous region") can be used to provide shorter term release of the second therapeutic agent. As noted above, the first and second therapeutic agents may be the same or different.

For example, taking a vascular stent as a specific example, the first and second therapeutic agents may correspond to a single antirestenotic agent, for instance, paclitaxel or one of the olimus family of therapeutic agents, among others.

Alternatively, first agent may be an anti-thrombotic or anti-inflammatory agent for slower release and the second therapeutic agent may be an antirestenotic agent for quicker release.

In some embodiments, crystalline regions may be provided which contain one or more particles of a first therapeutic agent in a predominantly crystalline form, while amorphous regions may be provided which contain one or more particles of a second therapeutic agent in a predominantly amorphous form. The particles may consist essentially of the first or second therapeutic agent or may further comprise an additional excipient material. Similarly, the crystalline and amorphous regions in these embodiments may consist essentially of such particles or they may further comprise an additional excipient material. In these embodiments, in addition to properties such as therapeutic agent crystallinity and amorphousness, release may be influenced by further properties such as particle size, the nature of the excipient material, if any, and therapeutic agent concentration. For example, the rate of therapeutic agent release is generally increased by decreasing particle size (because smaller particles have higher surface area per unit mass than larger particles) and/or by increasing therapeutic agent concentration (higher concentrations of therapeutic agent provide greater driving forces for diffusion than lower concentrations). The converse is also true. For instance, in some embodiments, particle size of a first therapeutic agent in a predominantly crystalline form may be maximized in size to favor delayed release, while particle size of a second therapeutic agent in a predominantly amorphous form may be minimized in size to favor burst release. In other embodiments, for example, large and small particles of a first therapeutic agent in a predominantly crystalline form may be employed to provide a bimodal release of the first therapeutic agent.

Several specific embodiments of the invention will now be described in conjunction with the drawings.

Turning now to FIG. 1, a schematic partial cross-section of a medical device in accordance with an embodiment of the invention is shown which includes a substrate 110, a first region 120c that comprises a first drug in predominantly crystalline form (i.e., a "crystalline region 120c") and a second region 120a comprising a second drug in predominantly amorphous form (i.e., an "amorphous region 120a"). As noted above, the first and second drugs may be the same or different. The crystalline region 120c may, for example, consist of a single crystal, a collection of crystalline particles (e.g., crystals), a collection of crystalline particles held together by a matrix of excipients, and so forth. Similarly, the amorphous region 120a may consist of a single particle of amorphous drug, a collection of particles of amorphous drug, a collection of particles of amorphous drug held together by an excipient matrix, and so forth. The crystalline region 120c and amorphous region 120a are disposed laterally with respect to one another on the surface of the substrate 110.

Figure 2:
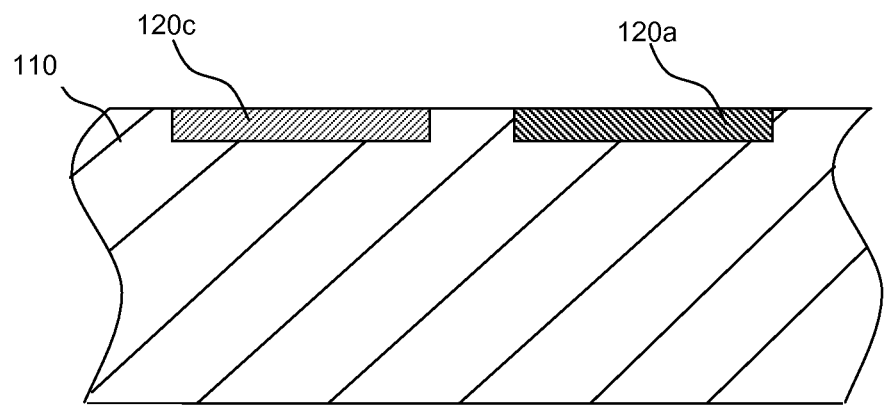

FIG. 2 is similar to FIG. 1 in that it illustrates a partial schematic cross-section of a medical device that includes a substrate 110 as well as an amorphous region 120a and a crystalline region 120c disposed laterally with respect to one another. However, in FIG. 2, the crystalline region 120c and amorphous region 120a are disposed within depressions in the substrate 110, rather the being disposed on the surface of the substrate.

Figure 3:
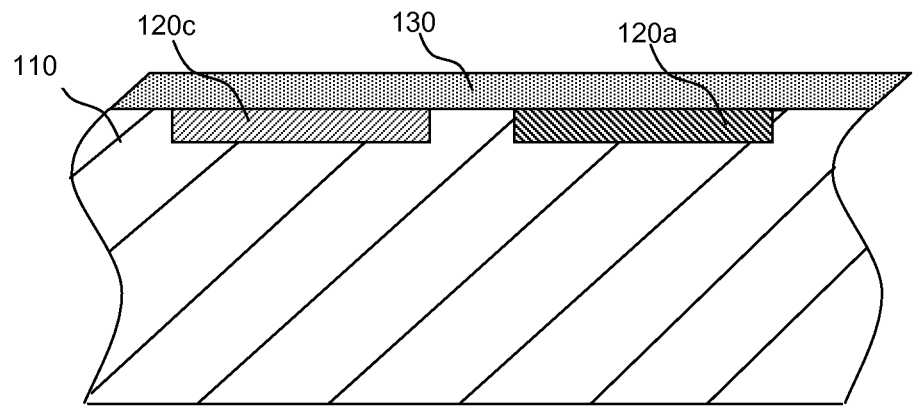
Figure 4:
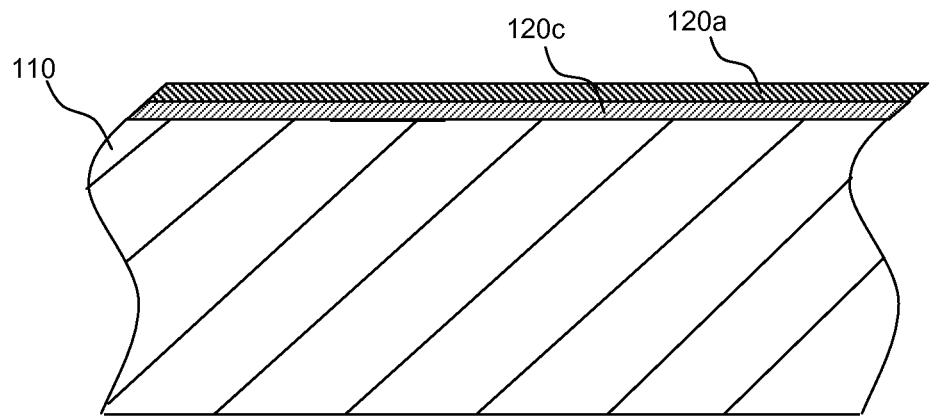

FIG. 3 is like FIG. 2, except that a release regulating layer 130, such as described above, is disposed over the amorphous region 120a and crystalline region 120c to further regulate the release of the therapeutic agents found in amorphous and crystalline regions 120a, 120c FIG. 4 is a schematic partial cross-section of a medical device in accordance with an embodiment of the invention which includes a substrate 110, an amorphous region 120a and a crystalline region 120c. Unlike FIGS. 1-3 above, rather than being disposed laterally with respect to one another, the crystalline region 120c and amorphous region 120a are disposed vertically with respect to one another (i.e., stacked) over the surface of the substrate 110. In the embodiment shown the amorphous region 120a is disposed over the crystalline region 120c, although the order can be reversed.

In FIGS. 1-4 only a single amorphous region 120a and a single crystalline region 120c are shown. In various embodiments of the invention, a plurality of regions 120a, 120b are employed.

Figure 5:
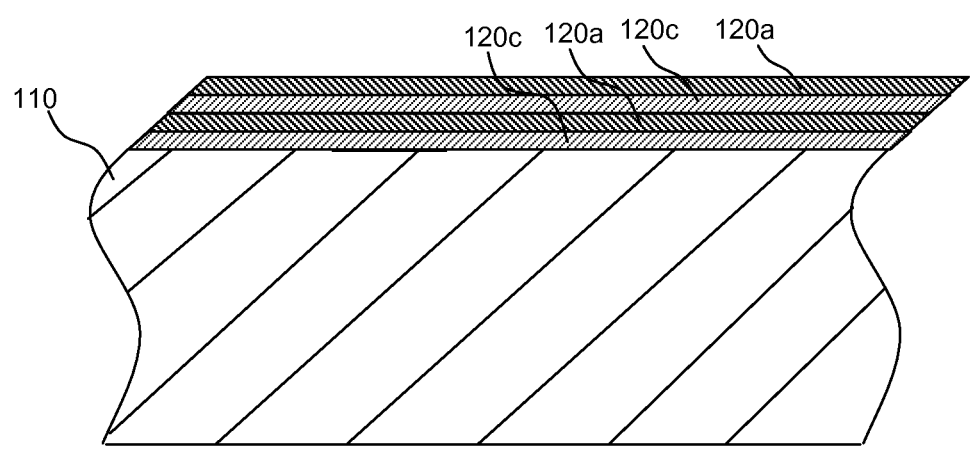

For example, FIG. 5 is a schematic partial cross-section of a medical device in accordance with an embodiment of the invention which includes a substrate 110, two amorphous regions 120a and two crystalline regions 120c. The crystalline regions 120c and amorphous regions 120a are disposed vertically with respect to one another (in an alternating stacked arrangement) on the surface of the substrate 110.

Figure 6:
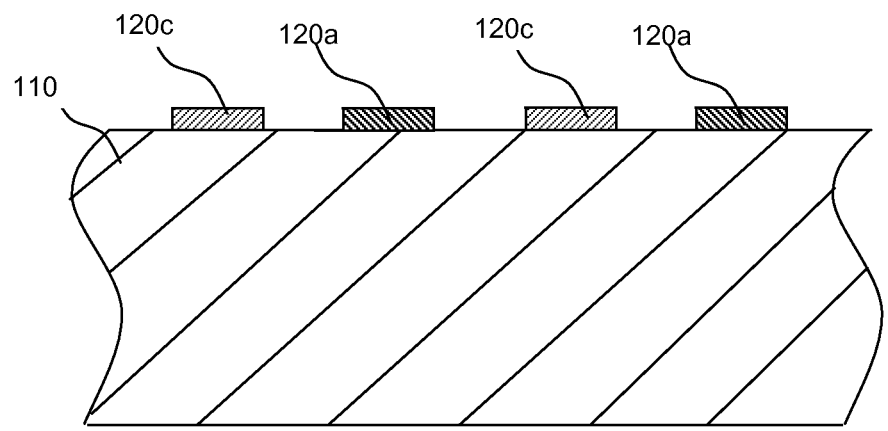

FIG. 6 is a schematic partial cross-section of a medical device in accordance with an embodiment of the invention which illustrates a substrate 110, two amorphous regions 120a, and two crystalline regions 120c. The crystalline regions 120c and amorphous regions 120a are disposed laterally with respect to one another (in an alternating arrangement) on the surface of the substrate 110. The crystalline regions 120c may be, for example, two regions out of many regions forming a patterned, discontinuous layer. Similarly, the amorphous regions 120a may be two regions out of many regions forming a patterned, discontinuous layer. The two patterned, discontinuous layers are interlocking.

Figure 7:
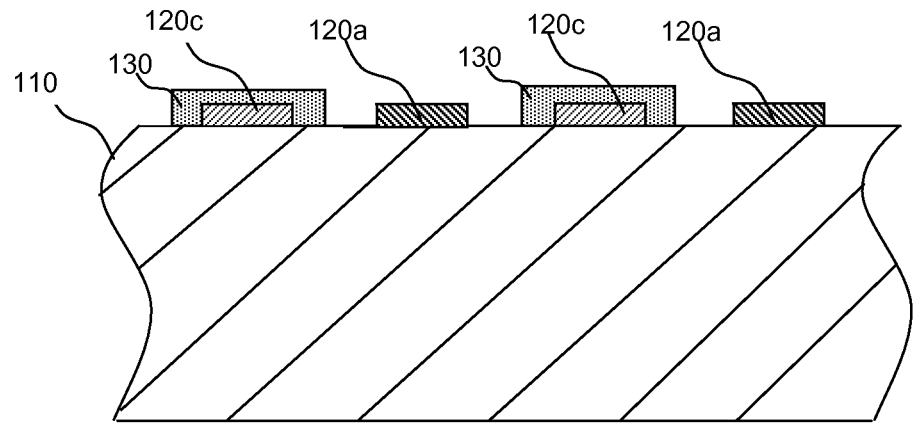

FIG. 7 is like FIG. 6 in that it is a schematic partial cross-section of a medical device in accordance with an embodiment of the invention which illustrates a substrate 110, two amorphous regions 120a, and two crystalline regions 120c. However, in FIG. 7, release regulating regions 130 are disposed over the crystalline regions 120c to further delay the release of the therapeutic agent disposed therein. In the embodiment shown, no release regulating regions 130 are disposed over the amorphous regions 120a to maximize release of the therapeutic agent therein.

Figure 8:
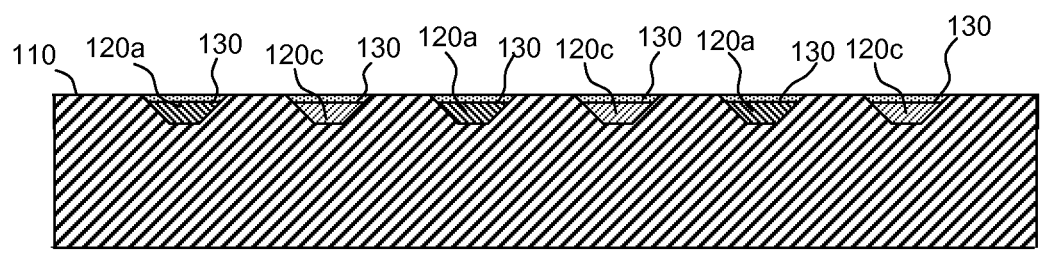
FIGS. 8, 11 and 12 schematic cross-sections of medical devices in accordance with various additional embodiments of the present invention.

FIG. 8 is a schematic cross-section of a medical device (e.g., a stent strut, etc.) in accordance with an embodiment of the invention and shows a substrate 110, three amorphous regions 120a and three crystalline regions 120c. The crystalline regions 120c and amorphous regions 120a are disposed laterally with respect to one another (in an alternating arrangement) within depressions in the substrate 110. Release regulating regions 130 are disposed over the amorphous regions 120a and crystalline regions 120c within the depressions.

Figure 9:
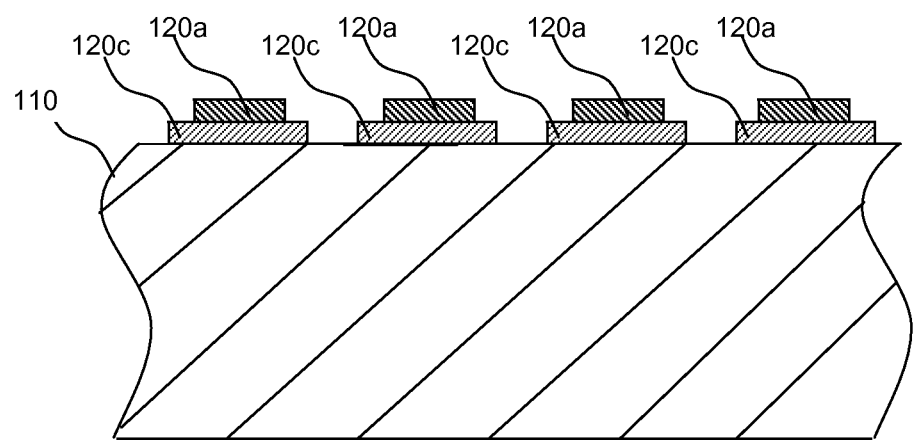

FIG. 9 is a schematic partial cross-section of a medical device in accordance with an embodiment of the invention and shows a substrate 110, and four amorphous regions 120a disposed over four crystalline regions 120c. The crystalline regions 120c are disposed laterally with respect to one another and form a patterned layer, as do the amorphous regions 120a.

Figure 10:
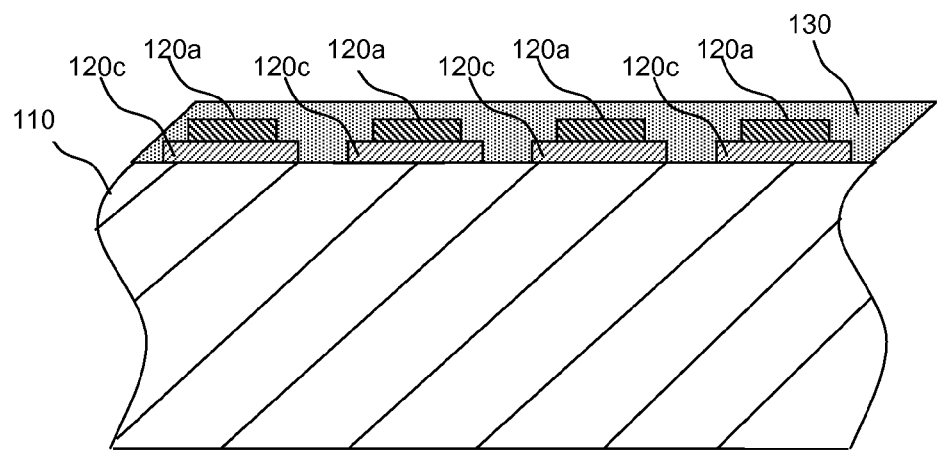

FIG. 10 is like FIG. 9, except that a release regulating layer 130 is disposed over the amorphous regions 120a and crystalline regions 120c to further regulate the release of the therapeutic agents found in these regions.

Figure 11:
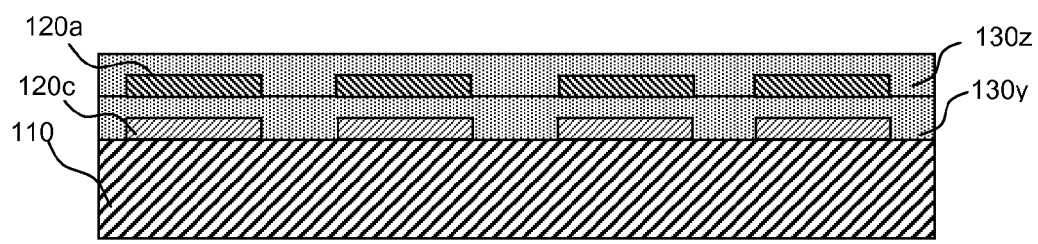

FIG. 11 is a schematic cross-section of a medical device in accordance with an embodiment of the invention and shows a substrate 110, and four amorphous regions 120a disposed over four crystalline regions 120c. The crystalline regions 120c are disposed laterally with respect to one another and form a patterned layer, as do the amorphous regions 120a. A first release regulating layer 130y is disposed over the crystalline regions 120c and under the amorphous regions 120a. An additional regulating layer 130z is disposed over the amorphous regions 120a, the first release regulating layer 130y and the crystalline regions 120c.

Figure 12:
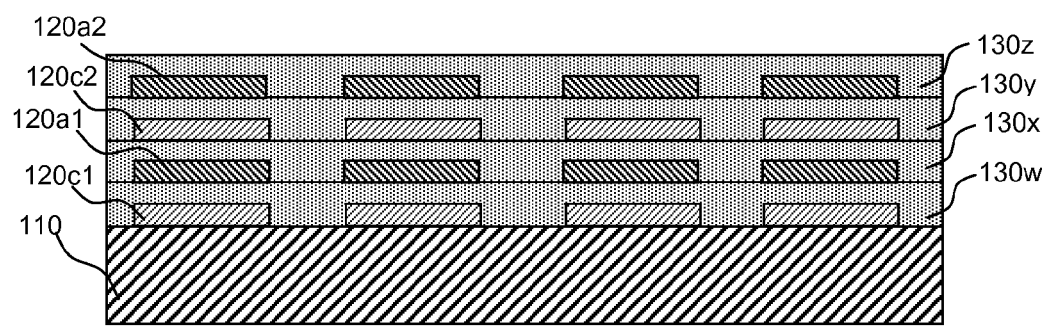

FIG. 12 is a schematic cross-section of a medical device in accordance with an embodiment of the invention and shows a substrate 110, over which is disposed, in order, a first patterned amorphous layer containing four amorphous regions 120a1, a first release regulating layer 130w, a first patterned crystalline layer containing four crystalline regions 120c1, a second release regulating layer 130x, a second patterned amorphous layer containing four amorphous regions 120a2, a third release regulating layer 130y, a second patterned crystalline drug layer containing four crystalline regions 120c2, and a fourth regulating layer 130z.

Clearly innumerable other embodiments are possible.

Crystalline and amorphous regions may be formed in various ways. In some embodiments, a drug material is pre-formed as required (e.g., in predominantly crystalline or predominantly amorphous form) and then applied to a substrate (either with or without an accompanying excipient material) to produce different layers or lateral regions of predominantly crystalline or predominantly amorphous drug material. Alternatively, medical device coating processes can also be manipulated to produce different layers or lateral regions of predominantly crystalline or predominantly amorphous drug material. As indicated above, alternating layers of crystalline and amorphous regions are possible.

As one specific example, an amorphous drug can be laid down using quick drying solvents on the surface of a stent in a predefined pattern. The drug can then be over coated with a porous layer (e.g., a non-polymeric porous ceramic or metallic layer) in some embodiments, producing a release regulating layer with pores, which layer will strongly adhere to the stent and secure the drug to the stent. Crystals of drug can then be laid down on top of this layer using a non-solvent for the drug that contains pre-formed drug crystals. The non-solvent randomly distributes the crystalline material on top of the porous layer without dissolving the crystals, and the crystals adhere enough to allow them to be over-coated with an additional porous layer.

With regard to drugs in predominantly crystalline form, the growth of sizeable drug crystals can be encouraged in a number of ways, with "the slower the better" being a general rule of thumb. Drugs in predominantly amorphous form can be produced using the opposite approach.

A good example is a spraying process for stents in which a drug containing solution is sprayed on a stent substrate. The slower the solvent is removed (e.g., by evaporation), the longer the drug region has to nucleate and grow and form crystals of drug. If one accelerates the evaporation process, the drug has less chance to nucleate and will precipitate in a random manner and will produce a predominantly amorphous drug material.

Drug particles may be formed by employing solvent-based processes whereby a solvent (which may contain one or more solvent species) is removed to produce drug particles. Combinations of two or more solvent species can also be used to vary solubility and evaporation parameters and produce amorphous and/or crystalline materials as desired.

For instance, one can form amorphous drug particles by employing solvent-based processes, such as spraying processes, whereby solvent is nearly instantaneously removed from the drug (e.g., by employing a heated substrate, vacuum conditions, low boiling solvent, etc.).

One can also form crystalline drug particles (i.e., drug crystals) using various solvent-based techniques. For example, slow evaporation of the solvent is a common way of encouraging crystal growth. Tightly controlling the rate of solvent evaporation encourages the growth of few large crystals, rather than many small ones. For example, in one procedure, a substantially saturated drug solution may be transferred to clean vial. (One should use glassware in crystallization procedures that is as clean and smooth as possible—old, scratched vessels provide a greater number of nucleation sites for crystals and tend to lead to the formation of microcrystalline compounds.) The vial is then covered, for example, using Parafilm®, aluminium foil, or some other covering, and a very small hole is pierced in the covering. The vial is then allowed to stand undisturbed as the solvent slowly evaporates, forming crystals.

Another way of encouraging crystal growth is via solvent cooling. Solvent cooling takes advantage of the fact that substances tend to be more highly soluble in hot solutions than in cold ones. Crystal formation is encouraged when the cooling is as slow as possible. For example, in one procedure, a substantially saturated drug solution in hot solvent is prepared, transferred to a vial and covered. The vial is then allowed to cool, for example, by placing it on a table top and allowing it to cool or by placing it in a temperature controlled environment (e.g., temperature controlled bath) and reducing the temperature in a controlled manner. As the solution cools, it becomes supersaturated, eventually leading to crystal growth upon nucleation.

An alternative procedure is to prepare a room-temperature solution in a low-freezing solvent and placing it in a depressed temperature environment (e.g., by storing it in a freezer), reducing the temperature in a controlled fashion, if desired.

In another procedure, a medical device substrate (e.g., a metallic stent) is chilled (e.g., by placing it on a cooled mandrel) and then immersed in a heated drug solution (e.g., a saturated solution of an anti-restenotic drug such as paclitaxel, etc.). By virtue of the temperature differential, drug crystals will grow outward from the substrate surface as the drug precipitates on the cooled stent while remaining dissolved in the heated solution.

Another way of encouraging crystal growth is through vapor diffusion. For this method two miscible solvents are used—one in which the drug is very soluble and one in which the drug is highly insoluble, referred to herein as an "anti-solvent" (e.g., a combination of polar and non-polar solvents is typically used; ether and hexane are a common initial choice). For example, in one method, a substantially saturated solution is prepared and place in a vial. This vial is then placed inside a larger vial which contains an anti-solvent. The larger vial is sealed. The anti-solvent may condense inside the smaller vial after a time and begin to mix slowly with the solution. Because the sample is insoluble in the condensing solvent, crystals form at the interface.

For example, for paclitaxel crystal formation, one could use chloroform as the solvent and hexane as the anti-solvent. See, e.g., In-Hyun Lee et al., *Journal of Controlled Release*, 102 (2005) 415-425. Processes for the production of drug crystals such as paclitaxel using anti-solvent methods are also described in U.S. Pat. No. 6,221,153 to Castor et al.

Yet another way of encouraging crystal growth is by anti-solvent diffusion. This technique is similar to vapor diffusion, requiring two contrasting solvents, except that a single vial is used. For example, in one technique, a substantially saturated solution is prepared and place in a vial. Then, an anti-solvent is carefully layered on top of the saturated solution. As the solvents mix, crystals form at the interface.

Further methods are directed to ways of forming drug crystals on a medical device surface. These methods allow control of the size and distribution of the crystals on the surface and therefore the elution rate and amount of therapeutic delivered to body. These methods also allow for a layer of discrete crystals (i.e., crystalline regions) to be formed on the device surface with bare substrate exposed between the crystals, enabling bonding between the substrate and any coating (e.g., a porous coating) that may be subsequently applied to control drug elution and/or hold the particles in place. The drug is preferably deposited in a controllable way such that a relatively precise drug dose is deposited in the form of discrete crystals of determinable size.

As above, drug crystal growth on substrates may be based upon a variety of methods including solvent evaporation (e.g., where a device is coated with a drug solution that is allowed to dry at a controlled rate), solvent cooling (e.g., where a device is contacted with a saturated solution, which is allowed to cool, thereby forming drug crystals), mixing with an anti-solvent (e.g., where a device is coated with a saturated solution, after which an anti-solvent is applied, causing the drug to come out of solution and form crystals), and so forth.

A specific example of an evaporation-based technique involves controlled removal of a medical device from a substantially saturated solution. For instance, a stent may be fixed in a cylindrical vessel such as a burette and the solution allowed to drain slowly away; the headspace contains vapor, which reduces the evaporation rate and allows uniform crystal growth.

It is well know that crystal nucleation initiates at imperfections or areas of roughness on a surface. By controlling the distribution of these nucleation sites, the distribution of the drug crystals can be controlled. A properly electropolished device is very smooth and unlikely to provide significant nucleation sites for crystal growth. Thus, such a device may act as a 'blank canvas' upon which nucleation sites may be created. Creation of nucleation sites can be accomplished in several ways.

As a first example, a medical device may be coated with inorganic nanoparticles with a sparse distribution. For example, the above-described system from Mantis Deposition Ltd. may be used to deposit metallic nanoparticles on a device surface. The amount, size, and morphology of nanoparticles on the medical device surface can be controlled by this method, allowing control of drug crystal distribution. For example, the result of this process is shown schematically in the left-hand portion of FIG. 13, which shows a medical device substrate 110 (e.g., a metallic device substrate) having a smooth electropolished surface 110e, within which are implanted/embedded metallic nanoparticles 140. Referring to the right-hand portion of FIG. 13, upon exposure to a drug containing solution 200 (followed, for example, by evaporation, cooling, etc.), the nanoparticles act as nucleation centers for the growth of drug crystals 120c.

In a more specific example, paclitaxel crystals may be provided on a stent surface for purposes of providing long term (e.g., 6 month) paclitaxel elution. For an 8 mm stent, an estimated 5.5 µg of paclitaxel is required. This is equivalent to $9 \times 10^8$ cubic particles of 200 nm side, or 16 of these particles per $\mu m^2$ of stent surface. A deposition system like the above-described system from Mantis Deposition Ltd. is used to deposit metal nanoparticles at this density on the stent surface. The stent is then exposed to a drug containing solution under conditions suitable for forming crystals (e.g., by spraying the stent with a solution of the drug and allowing it to dry very slowly). Crystals form at the impact sites of the deposited metal nanoparticles.

As another example, localized laser ablation or heating may be used to create centers for drug nucleation (e.g., by creating localized areas of roughness or changes in the grain structure at the device surface). Fast pulsed lasers may be used to roughen small areas (e.g., <1 micron).

As another example, an acid may be locally applied to certain areas of the device surface, resulting in localized acid etching and nucleation site creation.

As yet another example, parameters may be adjusted when electropolishing to create pits in the device surface for nucleation.

As still another example, the medical device surface may be mechanically scratched in localized areas to create nucleation sites.

As another example, the medical device surface may be pre-seeded by nano-sized or micro-sized crystalline or amorphous drug particles by coating the device in a dilute suspension of the drug particles (e.g., by suspending them in an anti-solvent). The device is then exposed to crystal growing methods such as those above (e.g., based on exposure to a saturated drug solution), causing crystals to form at the drug particles already on the surface.

In various embodiments, drug crystals are grown in controlled circumstances (e.g., within a vial or other controlled environment as described above) so that their size and crystal form can be chosen precisely. In some embodiments, large crystals of drug are milled (e.g., by ball milling) into a pre-determined range of particle sizes. The pre-formed crystals are then deposited onto the device surface. For example, drug crystals can be suspended in an anti-solvent and then applied to the device (e.g., sprayed, dipped, or deposited in drops, for instance, using techniques such as those above, including ink jet droplet deposition, microcontact printing, nanopipetting, dip pen nanolithography, the Nano eNabler™ system, etc.), resulting in a distribution of drug crystals in those area where the suspension is applied. The suspension may require an additive to prevent agglomeration. As another example, the particles are attached electrostatically to the device by suspending the particles in a stream of air (or another gas) and exposing the device to the airflow. The forgoing methods can also be used to deposit predominantly amorphous particles as well.

In another example, a solution of drug and polymer is sprayed on a substrate forming a coating that comprises drug particles within a polymer matrix. The matrix can then be removed using a solvent that dissolves the polymer but not the drug. In some embodiments, the substrate is not a medical device substrate, in which case the particles (which may be predominantly crystalline or predominantly amorphous) may be harvested and used, for example, as described above. Alternatively, the coating can be formed on the medical device itself, such that drug particles remain after the polymer is removed.

Figure 14:
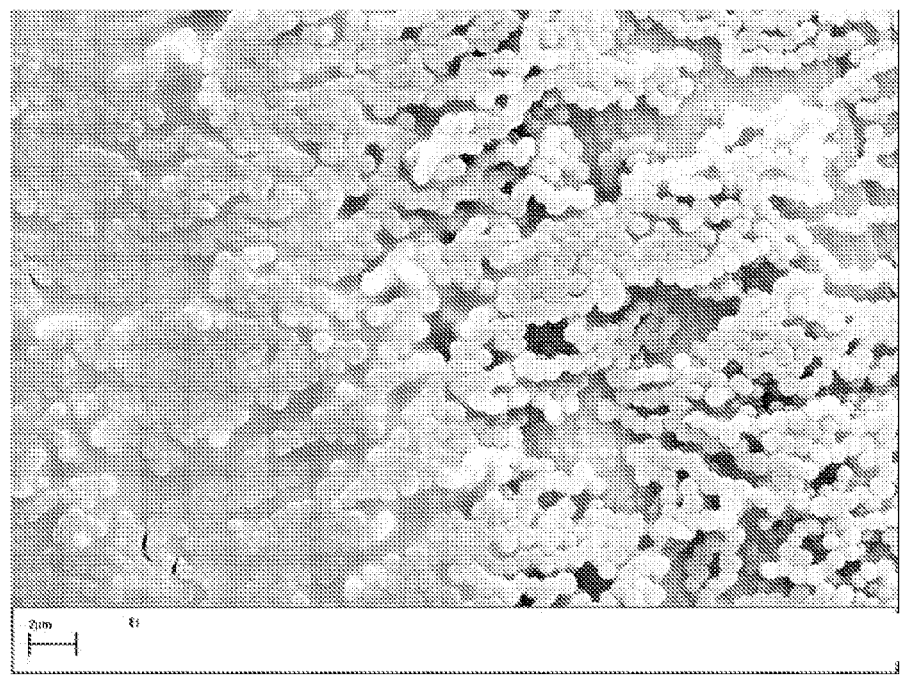
FIG. 14 is a scanning electron micrograph (SEM) of a coating of particles of paclitaxel within a poly(styrene-b-isobutylene-b-styrene) (SIBS) matrix, in accordance with an embodiment of the invention.

As a specific example, a solution containing 1 wt % solids in 99 wt % solvent, which solids consist of 50 wt % paclitaxel and 50 wt % SIBS (see, e.g., U.S. Pat. No. 6,545,097) can be spray coated on a medical device or other surface, yielding precisely sized crystalline paclitaxel particles in a SIBS matrix (see FIG. 14). The SIBS is then dissolved using a solvent that dissolves SIBS but not the paclitaxel particles (e.g., toluene).

As noted above, once a device is provided with drug particles on its surface, an organic or inorganic coating may be applied in some embodiments, for example, to firmly adhere the particles crystals to the surface and/or to reduce the rate of drug elution.

As also noted above, adhesion for subsequently applied coatings may be increased in some embodiments by providing a medical device substrate with a discontinuous layer of therapeutic-agent-containing material, which comprises a first area that corresponds to one or more regions of therapeutic-agent-containing material which cover the substrate and a second area which does not cover the substrate (i.e., leaving portions of the substrate bare). The therapeutic agent may be present, for example, in predominantly amorphous form, in predominantly crystalline form, or in a form that is neither predominantly amorphous nor predominantly crystalline.

Several techniques for forming a discontinuous layer of therapeutic-agent-containing material are described above. A further example of a technique for doing so is wherein the drug is deposited under conditions which lead to film boiling. "Film boiling" is a phenomenon that occurs when a droplet of drug solution is dispensed on a surface that is heated above the boiling point of the solvent species within the drug solution. When the droplet is dispensed on the surface, the solvent species within the liquid layer at the lower surface of the droplet is vaporized. The droplet is then carried on the vapor film for a short time, after which the solution again comes into contact with the surface, leading to the formation of another vapor film. The process is repeated until the droplet disappears. As a result of this process, the drug is deposited in rings of decreasing diameter, with the rings getting smaller as the droplet becomes smaller.

Figure 16:
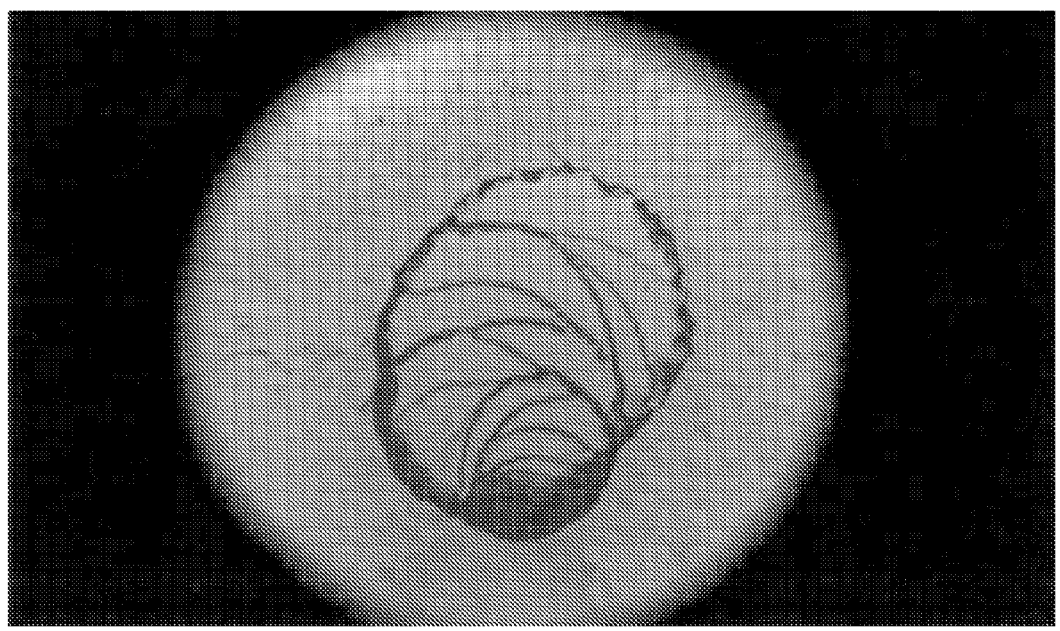
FIGS. 16 and 17 are scanning electron micrographs (differing magnification) of deposited paclitaxel on a stainless steel surface, in accordance with an embodiment of the invention.
Figure 17:
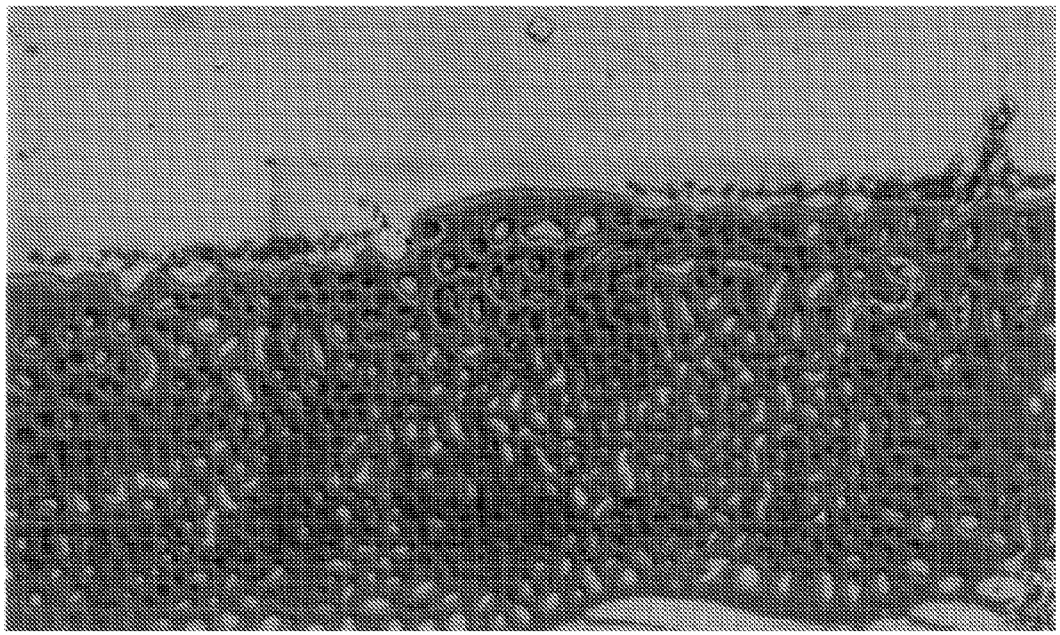

The result of such a technique is shown in FIG. 16, which is a scanning electron micrograph of a drug deposit that is formed by applying a droplet of paclitaxel dissolved in tetrahydrofuran (boiling point 66° C.) at a concentration of 0.01-0.1% onto a stainless steel substrate that has been heated to 70° C. As a result of the film boiling process, multiple rings are produced. FIG. 17 is a magnified view of a portion of FIG. 16. With a lower concentration of drug the deposits are thinner. Although the degree of crystallinity/amorphousness of the drug has not been measured, it is believed that the rings are predominantly amorphous due to the rapid rate at which the solvent was removed.

Figure 18:
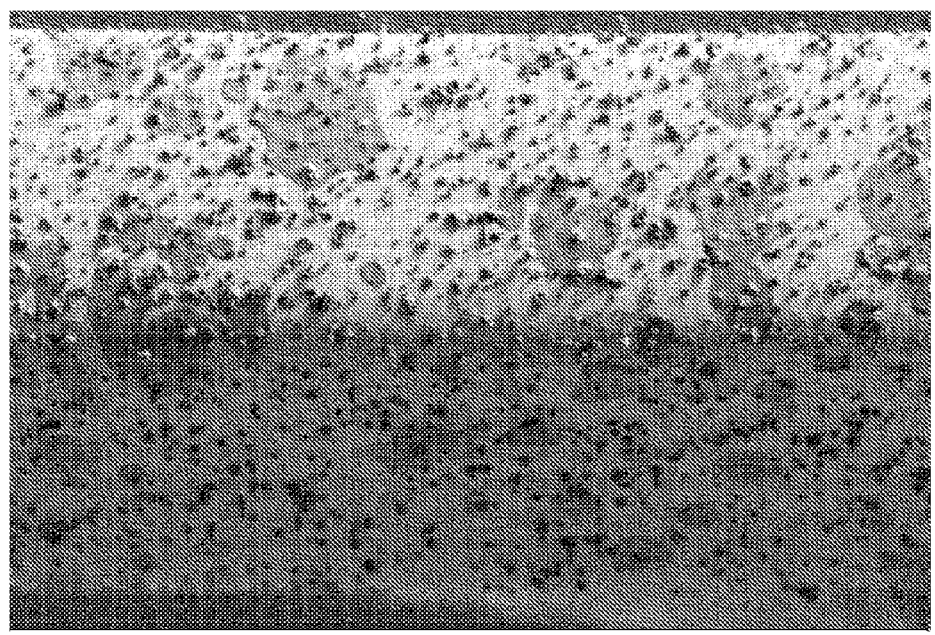
FIG. 18 is a scanning electron micrograph of a coating comprising particles of paclitaxel on a stainless steel stent surface, in accordance with an embodiment of the invention.

FIG. 18 illustrates a stent strut surface upon which is formed a single discontinuous layer of small (10-20 microns), loosely bound, sphere-like, randomly distributed particles of pure paclitaxel. Although the degree of crystallinity/amorphousness of the particles has not been measured, it is believed that the particles are predominantly amorphous due to the rapid rate at which the solvent is removed (~2-3 milliseconds). The important fact is that independent particles are formed. A process for forming the particulate layer of FIG. 18 is described in more detail below.

Figure 19:
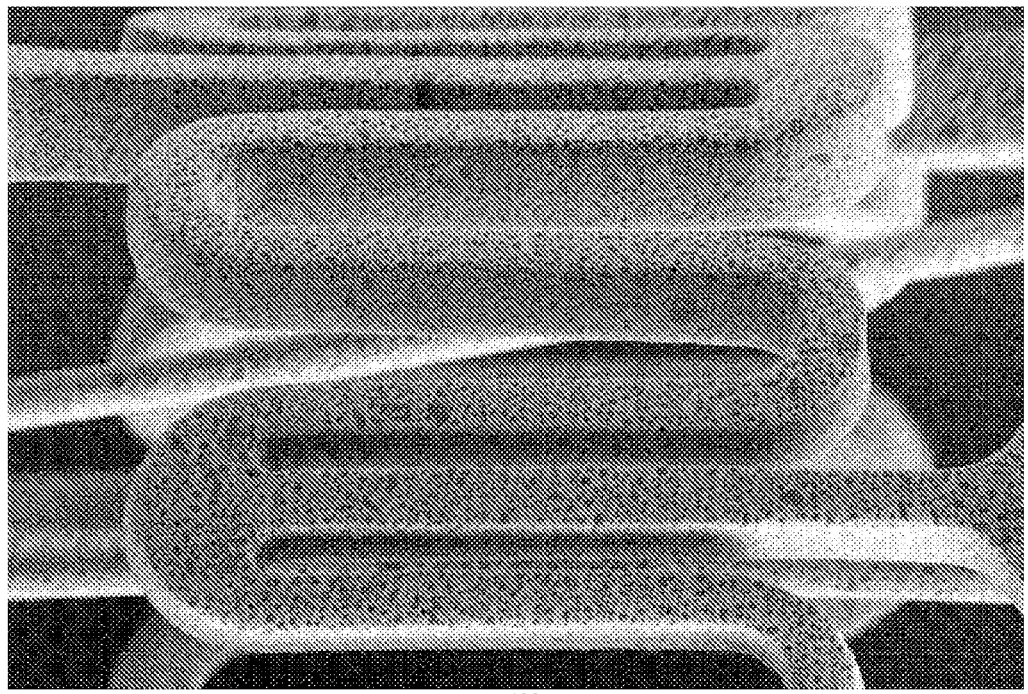
FIG. 19 is a scanning electron micrograph of a coating comprising dots of paclitaxel on a stainless steel stent surface, in accordance with an embodiment of the invention.

Raised particles like those shown in FIG. 18 can subsequently be modified (e.g., flattened) to produce particles like those shown in FIG. 19 by a solvent annealing process which will be described further below. As can be seen from the scale, the particles shown in FIG. 19 are less than 100 microns in width, more typically less than 50 microns, even more typically, less than 25 microns. The flattened particles of FIG. 19 have much greater interfacial contact with the substrate than the raised particles of FIG. 18, they have an excellent adhesion to the substrate, and they are robust when subjected to mechanical forces such as crimping and delivery.

Figure 22A:
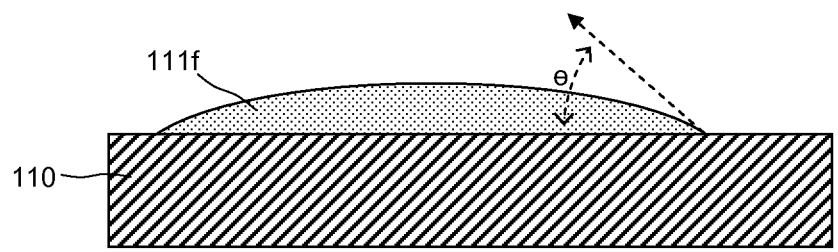
FIG. 22A is a schematic cross-sectional diagram illustrating a flattened particle in accordance with the present invention on a substrate.

In certain embodiments of the invention, flattened particles may be formed which have a contact angle $\theta$ with the substrate that is less than 90° (preferably 90° to 60° to 45° or less). For example, 75 wt % or more (preferably 75 wt % to 90 wt % to 95 wt % or more) of the particles may have such contact angles. FIG. 22A is a schematic cross-sectional diagram illustrating a flattened particle 111f in accordance with the present invention on a substrate 110. FIG. 22A also illustrates the contact angle $\theta$ between the particle and the substrate.

Figure 22B:
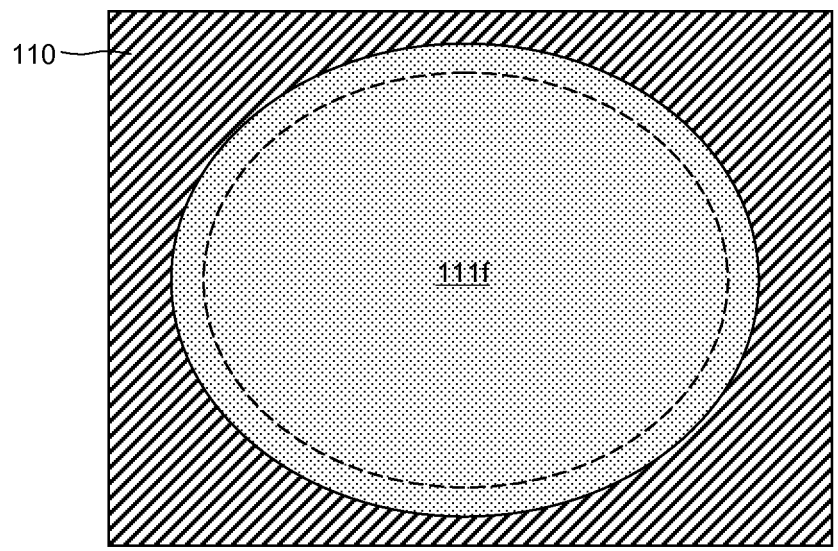
FIG. 22B is a schematic top view illustrating a flattened particle in accordance with the present invention on a substrate.

In certain embodiments of the invention, flattened particles may be formed in which the average height in the perimeter area of the particle (i.e., the 20% of the particle area that likes closest to the perimeter) is less that 75% of the average height in the remaining 80% central area of the particles. For example, 75 wt % or more (preferably 75 wt % to 90 wt % to 95 wt % or more) of the particles may have such characteristics. FIG. 22B is a schematic top view illustrating a flattened particle in accordance with the present invention on a substrate. The 80% central area (not exactly to scale) of the flattened particle 111f is designated by the area within the dashed oval, whereas the 20% perimeter area is the area outside the dashed oval.

Note that, although the drug particles of FIGS. 18 and 19 are disposed on a metallic stent, such layers may be disposed on devices other than stents (e.g., balloons, among others described herein) and on materials other than metals (e.g., polymers, among others described herein).

Like FIGS. 16 and 17, the layers shown in FIGS. 18 and 19 are discontinuous layers and may thus be desirable in that any subsequently applied coating can be in direct contact with the substrate and may thus exhibit enhanced adhesion in some embodiments.

The particulate layer of FIG. 18 may be desirable in certain embodiments, because the raised particles of that layer may promote damage to an overlying release regulating layer (e.g., a non-porous biostable layer) under compression (e.g., for a stent, upon engagement with surrounding tissue), allowing the layer to be breached and facilitating therapeutic agent release. Conversely, the particulate layer of FIG. 19 may be desirable in certain embodiments, because the flat smooth particles of that layer may protect an overlying release regulating layer (e.g., a porous layer or a biodisintegrable layer) from damage during compression.

Layers of discrete small particles such as those shown in FIGS. 18 and 19 may also be advantageous in that small particles may provide for reduction/elimination of embolization risk relative to continuous coatings, which may undergo peeling in vivo.

Layers of discrete small particles may also exhibit enhanced substrate adhesion (relative to continuous coatings) under circumstances where the substrate is subjected to variable strain during device deployment. This attribute of small particles is particularly desirable for particulate layers such as those of FIG. 19, which in general have excellent adhesion to the stent surface. In this regard, due to the large deformations of devices such as stents during introduction and after implantation, it has been customary to apply the drug in conjunction with a polymer matrix that is able to follow these deformations. The use of small, well adhering particles such as those shown in FIG. 19 allows the polymer matrix (whose only function is to hold and elute the drug) to be eliminated, thereby allowing a polymer-free device to be formed.

Small particles may also undergo direct cellular uptake if the particles are properly sized (e.g., in the range of 10-50 um). This attribute of small particles is particularly desirable for particulate layers such as those of FIG. 18, which are loosely bound and would be quickly released for tissue uptake in vivo (e.g., upon stent expansion). See also FIG. 21 below, in which particles may be disposed over dissolvable organic material layers. Upon dissolution of the organic layers, the particles will be released for tissue uptake in vivo.

Layers of discrete small particles such as those shown in FIGS. 18 and 19 are also amenable to further processing by which a portion of the particles are removed. For example, one may wish to remove a portion of the particles in order to achieve a total therapeutic agent dosage for the device. In other words, one may deposit therapeutic agent on the device in an amount somewhat exceeding the target amount, followed by removal of particles to achieve the target amount.

As another example, while particles of therapeutic agent may be highly desirable on certain surface of a medical device, they may be less desirable on other surfaces. For instance, with regard to vascular stents, it may be desirable to provide an anti-proliferative drug on the abluminal (vessel wall contacting) surface of the stent to prevent excessive smooth muscle cell growth (which can cause vessel narrowing or restenosis). However, such a drug may be undesirable on the luminal (blood contacting) surface of the stent or the intermediate surfaces of the stent between the luminal and abluminal surfaces (e.g., the laser cut surfaces), because the drug can inhibit endothelial cell growth, which is desirable on such surfaces. In these instances, one may wish to leave the particles on the abluminal surface, but remove particles on the luminal and intermediate surfaces (the luminal surface may also be masked, e.g., by a mandrel to prevent particle deposition). One may also wish to remove a portion of the particles on the abluminal surface such that only a line of particles remains in the central portions of the stent struts.

Particles may be removed, for example, using a focused ablating laser. Where only a portion of a drug-containing region is removed by laser ablation, the question may arise regarding whether or not the border of the ablated areas might contain undesirable reaction products (due to the high ablation temperatures). In the case of discrete drug-containing particles, however, the entire particle can be ablated without the creation of such border regions and without affecting surrounding particles.

In some embodiments, one or more layers of drug-containing particles may be combined with one or more layers of organic material which may, for example, assist with the release of the particles and/or allow multiple layers of particles to be deposited (thereby increasing dose per unit area), among other functions. Raised drug containing particles may be deposited within such a scheme, for instance, in accordance with the procedures described in FIG. 18, among others. Flattened drug particles may be deposited, for instance, as described in conjunction with FIG. 19, among others. (Note that solvent annealing will only affect the top layer of drug particles, any drug particles already buried beneath the organic layer(s) remain unaffected.) Organic layers may be formed by dissolving the organic material in a suitable solvent, which is preferably a poor solvent for any underlying drug particles (e.g., where one wishes to preserve the particle morphology). If desired, the organic layers themselves may be optionally treated using the solvent annealing process described herein. Examples of such organic materials may be selected, for example, from those listed above, among others.

For balloons, preferred organic materials include organic materials which (a) are able to dissolve quickly in vivo and release the drug particles (which as noted above may exhibit enhanced tissue uptake) and/or (b) are hard and brittle. Hard, brittle materials are those which form cracks and delaminate from an underlying radially expandable substrate (e.g., balloon or stent) upon deployment. For example, a fully coated folded balloon may be fully deployed by inflation to 18 atm. at 37 C for 60 seconds within a saline environment. The surface of the coated layer is inspected by microscope after the expansion procedure and the coated (i.e., non-delaminated) surface area is measured. When the coated surface area is less than 60%, the coating as such is defined as a "hard, brittle" coating. Note that in the case of a balloon material, this procedure involves inflation from a folded state to a fully deployed round structure. Furthermore, when the pressure in a balloon material is raised from 6 atm. up to 18 atm., even balloon materials defined as "non-compliant" tend to expand in diameter (typically by 10% or more) causing sufficient stress at the interface of the layer. The delamination of the top-coating is therefore caused by a complex combination of geometrical transformation (folded to round) and significant stress formation at the interface. Without wishing to be bound by theory, it is shown that a layer of this type is able to break into fragments upon device expansion, thereby increasing the rate of drug release from the device. It is believed that such brittle fragments may penetrate the surrounding tissue (e.g., vessel wall) upon device expansion, thereby enhancing drug delivery to the surrounding tissue.

Specific examples of organic materials that (a) are able to dissolve quickly in vivo and/or (b) are hard and brittle, include sugar alcohols (e.g., mannitol, etc.), sugar phosphate and sugar sulfate, sugars, for example, mono- and di-saccharides such as glucose (dextrose), fructose (levulose), galactose, xylose and ribose, sucrose, lactose and maltose, and contrast media such as iopromide and iobitridol, iohexyl, iomeprol, iopamidol, iopentol, iopromide, ioversol, ioxilan, iotrolan, iodixanol, ioxaglate, and their derivatives.

Figure 21:
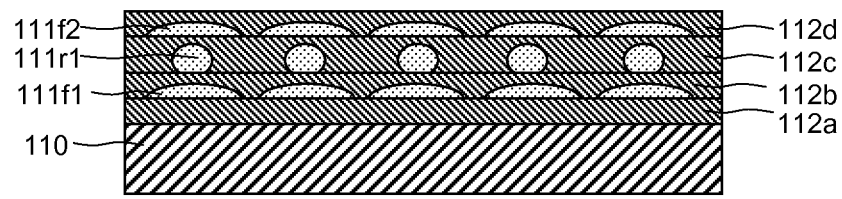
FIG. 21 is a schematic cross-sectional illustration of a medical device with alternating organic and particulate layers, in accordance with an embodiment of the invention.

A schematic cross-sectional illustration of a medical device with alternating organic and particulate layers is shown in FIG. 21. In particular, FIG. 21 illustrates a substrate 110 (e.g., a balloon, stent, etc.), a first organic layer 112*a* formed over the substrate region, a first layer of flattened particles 111*f*1 formed over the first organic layer 112*a*, a second organic layer 112*b* formed over the first layer of flattened particles 111*f*1, a first layer of raised particles 111*r*1 formed over the second organic layer 112*b*, a third organic layer 112*c* formed over the first layer of raised particles 111*r*1, a second layer of flattened particles 111*f*2 formed over the third organic layer 112*c*, and a fourth organic layer 112*d* formed over the second layer of flattened particles 111*f*2.

Although the preceding example concerned alternating layers of organic materials and drug-containing particles, such organic materials may also be combined with the drug and particles formed from the drug/organic material blend deposited on the substrate.

As noted above, FIG. 18 shows a single discontinuous layer of small (10-20 microns), loosely bound, sphere-like, randomly distributed particles of pure paclitaxel. FIG. 18 also includes a lesser number of larger flat paclitaxel deposits. With regard to processing, the layer of FIG. 18 can be formed by spraying a solution containing paclitaxel onto a stent under suitable conditions. To form a layer like that of FIG. 18, the stent is first sprayed with drug concentration of between 1-10% paclitaxel in THF (tetrahydrofuran). Process conditions are varied to achieve the required weight (which can be measured by weighing afterward). Process parameters varied are nozzle flow rate (10-30 ml/hr), atomizing gas pressure (5-30 psi), nozzle distance from the stent (10-100 mm), rotational speed of the stent (10-80 RPM), stent linear motion (1-20 mm/s) For another anti-restenotic agent such as everolimus, the same conditions may be employed, which except that the solvent used in the solution for spraying the stent would preferably be an acetone and cyclohexanone mixture, but could also be THF.

As noted above, raised particles can subsequently be modified (e.g., flattened) to produce particles like those shown in FIG. 19 by a solvent annealing process which will now be described. Although the particles that are solvent annealed in FIG. 19 are prepared using a solvent spraying process like that described in conjunction with FIG. 18, particles deposited by any other method may be solvent annealed as well. As one specific example among many, drug particles may be formed by depositing arrays of small drops of a fluid containing a drug (e.g., in dissolved or dispersed form) using a device such as the Nano eNabler™ as described above. Such methods are desirable in that drug may be placed in desired positions (e.g., on the abluminal surface of a stent only) and in precise quantities.

In the solvent annealing process, drug particles are exposed to a gaseous atmosphere that contains a solvent within which the drug particles are soluble. The solvent may be composed of a single solvent species or mixture of solvent species. By "soluble" is meant that the drug particles can be dissolved in the solvent in a concentration of at least 0.01 g/ml. Solubility depends, of course, on various parameters and theory and experimental data can be found for example in the IUPAC-NIST Solubility Database as provided by the Measurement Services Division of the National Institute of Standards and Technology (NIST). Without wishing to be bound by theory, is believed that liquid solvent accumulates (e.g., via adsorption, absorption, condensation, etc.) at the device surface (or at least at the drug particles), thereby wetting the particles and allowing the therapeutic agent molecules within the particles to migrate along the device surface (e.g., via dissolution of the therapeutic agent molecules). This allows the particle material to flow, and in some instances, the particle material may undergo rearrangement, for example, whereby the particle material from adjacent particles combines, whereby particle material within a single particle segregates, and so forth.

In some embodiments, the surface of the stent is non-homogeneous, with the particle material preferentially remaining within or flowing into certain regions of the stent surface relative to others. Such "attractor" regions may be, for example, more hydrophobic, more hydrophilic or have increased roughness relative to adjacent areas. Such areas may be formed, for example, by laser engraving and/or polishing. For example, the stent struts may be subjected to laser treatment to form attractor regions in the form of lines or dots which attract drug droplets during solvent annealing.

A simple system for solvent annealing may include a sealed chamber containing a solvent containing atmosphere. Such an atmosphere may be formed, for example, by allowing a pool of solvent in an air-filled chamber to come to equilibrium (saturation) at a given temperature (e.g., room temperature or above). Upon introduction of the device to the chamber, the solvent may wet the drug particles, leading to drug dissolution and flow. The device is removed from the chamber after a desired period of exposure to the chamber atmosphere. Such a process may be implemented/accelerated where the equilibrium temperature in the chamber is greater than the temperature of the medical device upon introduction, in which case the device surface will be below the "dew point" of the saturated vapor.

Figure 20:
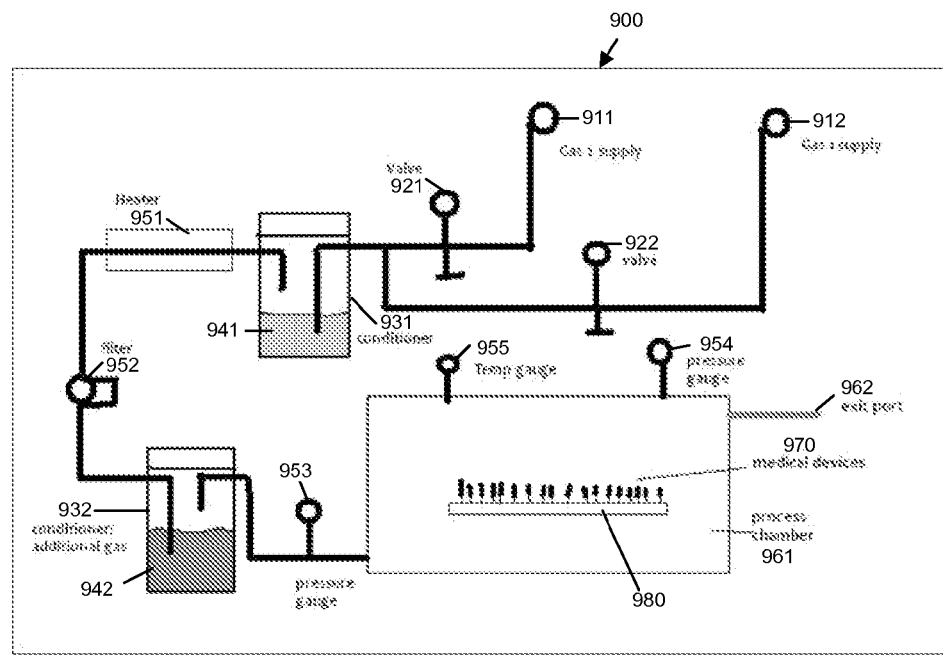
FIG. 20 is a schematic illustration of an apparatus in accordance with an embodiment of the invention.

More sophisticated systems, on the other hand, will allow for more process control. An example of such a system is shown in FIG. 20, which shows a schematic illustration of an apparatus 900 that includes two gas supplies 911, 912 (allowing for the use of multiple carrier gases) and valves 921, 922 for controlling the flow rate of the gas stream from the gas supplies 911, 912. The apparatus 900 further includes a first conditioner 931. The first conditioner 931 may be used, for example, to filter and remove water vapor from the gas stream from gas supplies 911, 912, for example by bubbling the gas stream through a liquid 941 such as liquid nitrogen. The apparatus 900 further includes a heater 951, through which the gas stream emerging from the conditioner 931 is passed to increase its temperature (heating encourages solvent evaporation in subsequent operations and thus can be used to increase the solvent concentration in the gas stream), and a filter 952, though which the heated gas stream is passed to remove any particulate that may be contained in the gas supply. A second conditioner 932 is also provided, with contains a solvent 942 (which can include one or more solvent species) through which the heated gas stream is bubbled to allow the gas stream to pick up solvent. The greater the path length for the gas bubbles, the greater the uptake of solvent molecules into the gas bubbles by evaporation. If desired, the gas stream can be bubbled through an additional solvent in an additional conditioner (not shown), which additional solvent may include one or more solvent species that can be the same as or different from the solvent species in solvent 942 of conditioner 932. The conditioned gas stream then flows into a process chamber 961 which contains medical devices 970 (e.g., stents or balloons with particulate drug coating like that of FIG. 18). Gas emerges from the chamber via exit port 962. The apparatus 900 shown also contains various sensors, including pressure gauges 953, 954 and a temperature gauge 955 for monitoring process conditions. If desired, the platform 980 upon which the medical devices 970 are mounted may be cooled to reduce the temperature of the devices relative to the process chamber. If desired, the medical devices may be mechanically agitated (e.g., by ultrasonic vibration, by rotation, etc.) during vapor exposure.

In some embodiments, an additional gas supply (now shown) may be provided which feeds gas into the chamber to purge the solvent vapor after a desired residence time. The gas from the gas supply may be heated and/or conditioned as desired. Further advanced equipment which can be used for improved control includes mass flow controllers, vacuum pumps, devices for chamber temperature control (e.g., heaters, coolers, etc), and so forth.

As noted above, the gas stream entering the chamber may include one or more solvent species. In this regard, some drug molecules have both hydrophobic and hydrophilic portions and may be dissolved more efficiently in a solvent containing two (or more) solvent species with different properties. Also, using differing solvent species, azeotropic mixtures of various solvent vapors may be created in certain embodiments of the invention. Such azeotropes may act as unique solvents, having differing solubilities and boiling points. This provides additional options when optimizing the system.

Process variables for the apparatus 900 of FIG. 20 include chamber temperature, chamber pressure, carrier gas composition (e.g., air, $O_2$, $N_2$, Ar, etc.) and flow rate, solvent vapor composition and concentration (with higher concentrations yielding faster results), and medical device exposure time, among others. Such factors may affect drug particle morphology and the degree of crystallinity, if any (e.g., slower morphology changes may potentially lead to the creation of crystallinity). Accordingly, different drug polymorphs may be formed and controlled using these factors.

In some embodiments of the invention, solvent annealing may be used to change the morphology/nature of (e.g., flatten, render more crystalline, etc.) particles of one drug on a medical device surface without significantly changing the morphology/nature of another drug. For example, such a procedure may be formed using a solvent that is a non-solvent for one of the drugs but a good solvent for the other. For example, water is a poor solvent for paclitaxel (particularly crystalline, non-hydrated paclitaxel) but a good solvent for a drug such as sodium heparin. Therefore, a high humidity environment may be used to dissolve sodium heparin particles and change their morphology/nature, while high humidity would have a less significant effect on paclitaxel particles. As another example, chloroform is a good solvent for paclitaxel but not a good solvent for warfarin. Thus, chloroform may be used to dissolve the paclitaxel particles while having a less significant effect on the warfarin particles. For a given pair of drug particles, relative solubilities in various solvents (e.g., organic solvents such as acetone, DMSO, alcohols, chloroform, ethers, weak acids, etc.) may be assessed (e.g., via literature survey, experimentally, etc.), with those solvents providing the greatest differences in relative solubilities being used to selectively change the morphology/nature of particles of one drug but not the other. In some embodiments, the solubility differential between two drugs may be achieved/enhanced by conjugating one or the drugs to another entity. For example, a hydrophobic drug may be conjugated to a hydrophilic entity or vice versa to change its solubility.

In accordance with one particular embodiment of the invention, flattened particles such as those shown in FIG. 19 are formed by exposing a device like that of FIG. 18 to a solvent vapor mixture of acetone and THF (1:1) for 20-120 seconds. The temperature is room temp (21° C.). The solvent vapor concentration is adjusted by varying the pressure of the nitrogen gas that is bubbled through the liquid solvent.

In another particular embodiment of the invention, flattened particles such as those shown in FIG. 19 are subsequently overcoated with a nanoporous inorganic layer (e.g., a nanoporous tantalum layer, etc.) For example, tantalum nanoparticles of 10 nm average diameter may be deposited to a layer thickness of 55 nm using the Nanogen 50 system from Mantis Deposition Ltd. at a setting of 1100 V, thereby creating a nanoporous outer tantalum film.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising an inorganic substrate, a discontinuous layer of therapeutic-agent containing material that comprises a therapeutic agent, said discontinuous layer comprising a first area corresponding to a plurality of regions of said therapeutic-agent-containing material which cover the substrate and a second area which does not cover the substrate, and an inorganic nanoporous layer disposed over the therapeutic-agent-containing layer, said inorganic nanoporous layer being in contact with said therapeutic-agent-containing material in said first area and in contact with said substrate in said second area, wherein said regions of said therapeutic-agent-containing material are not disposed within depressions in the surface of a substrate, and wherein said regions of said therapeutic-agent-containing material are in the form of discrete flattened particles.

2. The medical device of claim 1, wherein 75 wt % or more said flattened particles have a contact angle with the substrate that is less than 90°.

3. The medical device of claim 1, wherein said flattened particles are formed by a process in which particles of said therapeutic-agent-containing material are exposed to a vapor that comprises a solvent within which the particles are soluble under conditions such that the solvent wets the particles.

4. The medical device of claim 3, wherein the therapeutic-agent-containing material comprises at least 95% therapeutic agent.

5. The medical device of claim 3, wherein the medical device substrate is a balloon or a stent and wherein the therapeutic-agent-containing particles comprise an anti-restenotic agent.

6. The medical device of claim 5, wherein said medical device is a stent.

7. The medical device of claim 6, wherein said substrate is selected from titanium and its alloys, iron and its alloys, magnesium and its alloys, stainless steel and nitinol and wherein said inorganic nanoporous layer comprises a metal selected from tantalum, iron, magnesium, calcium, platinum, gold and combinations thereof.

8. The medical device of claim 6, wherein said discontinuous layer and said nanoporous layer are disposed over an abluminal surface of the stent but are not disposed over a luminal surface of the stent.

9. The medical device of claim 3, wherein 100% of particles are less than 100 micrometer in length and width.

10. The medical device of claim 3, wherein 90% of the particles are less than 20 micrometer in length and width.

11. The medical device of claim 1, wherein the therapeutic-agent-containing material comprises at least 95% therapeutic agent.

12. The medical device of claim 1, wherein the medical device substrate is a balloon or a stent and wherein the therapeutic-agent-containing particles comprise an anti-restenotic agent.

13. The medical device of claim 12, wherein said medical device is a stent.

14. The medical device of claim 13, wherein said substrate is selected from titanium and its alloys, iron and its alloys, magnesium and its alloys, stainless steel and nitinol and wherein said inorganic nanoporous layer comprises a metal selected from tantalum, iron, magnesium, calcium, platinum, gold and combinations thereof.

15. The medical device of claim 13, wherein said discontinuous layer and said nanoporous layer are disposed over an abluminal surface of the stent but are not disposed over a luminal surface of the stent.

16. The medical device of claim 1, wherein 100% of particles are less than 100 micrometer in length and width.

17. The medical device of claim 1, wherein 90% of the particles are less than 20 micrometer in length and width.

18. A medical device comprising an inorganic substrate, a discontinuous layer of therapeutic-agent containing material that comprises a therapeutic agent, said discontinuous layer comprising a first area corresponding to a plurality of regions of said therapeutic-agent-containing material which cover the substrate and a second area which does not cover the substrate, and an inorganic nanoporous layer disposed over the therapeutic-agent-containing layer, said inorganic nanoporous layer being in contact with said therapeutic-agent-containing material in said first area and in contact with said substrate in said second area, wherein said regions of said therapeutic-agent-containing material are not disposed within depressions in the surface of a substrate, and wherein said regions of said therapeutic-agent-containing material include a first region in which said therapeutic-agent-containing material is in the form of discrete spherical particles, and a second region in which said therapeutic-agent-containing material is in the form of discrete flattened particles.

19. The medical device of claim 18, wherein the therapeutic-agent-containing material comprises at least 95% therapeutic agent.

20. The medical device of claim 18, wherein the medical device substrate is a balloon or a stent and wherein the therapeutic-agent-containing particles comprise an anti-restenotic agent.

21. The medical device of claim 20, wherein said medical device is a stent.

22. The medical device of claim 21, wherein said substrate is selected from titanium and its alloys, iron and its alloys, magnesium and its alloys, stainless steel and nitinol and wherein said inorganic nanoporous layer comprises a metal selected from tantalum, iron, magnesium, calcium, platinum, gold and combinations thereof.

23. The medical device of claim 21, wherein said discontinuous layer and said nanoporous layer are disposed over an abluminal surface of the stent but are not disposed over a luminal surface of the stent.

24. The medical device of claim 18, wherein 100% of particles are less than 100 micrometer in length and width.

25. The medical device of claim 18, wherein 90% of the particles are less than 20 micrometer in length and width.

* * * * *